United States Patent [19]
Kampe et al.

[11] Patent Number: 5,587,476
[45] Date of Patent: Dec. 24, 1996

[54] FULLERENE DERIVATIVES, METHOD OF SYNTHESIZING THEM AND THEIR USE

[75] Inventors: Klaus-Dieter Kampe, Bad Soden am Taunus; Hans-Ulrich ter Meer, Frankfurt am Main; Norbert K. Egger, Wiesbaden; Martin A. Vogel, Nackenheim, all of Germany

[73] Assignee: Hoechst Aktiengesellschaft, Frankfurt, Germany

[21] Appl. No.: 381,946

[22] PCT Filed: Aug. 26, 1993

[86] PCT No.: PCT/EP93/02306

§ 371 Date: Feb. 15, 1995

§ 102(e) Date: Feb. 15, 1995

[87] PCT Pub. No.: WO94/05671

PCT Pub. Date: Mar. 17, 1994

[30] Foreign Application Priority Data

Sep. 8, 1992 [DE] Germany .......................... 42 29 979.9
Apr. 19, 1993 [DE] Germany .......................... 43 12 632.4

[51] Int. Cl.$^6$ ...................... C07D 241/38; C07D 243/10; C07D 245/04; C07D 487/06
[52] U.S. Cl. ...................... 540/472; 540/556; 544/338; 252/500
[58] Field of Search ........................ 544/338; 540/472, 540/556

[56] References Cited

FOREIGN PATENT DOCUMENTS

93/15768  8/1993  WIPO .

OTHER PUBLICATIONS

Kampe, Angew. Chem., 105(8), (1993), pp. 1203–1205.
Kampe, Angew Chem. Int. Ed. Engl, 32(8), (1993), pp. 1174–1176.
Wudl et al, Chemical Abstract 116:193407h (1992).
Kampe et al, Chem. Abstract 119:270776u (1993).
Haddon, R. C. et al., "Conducting films of $C_{60}$ and $C_{70}$ by alkali–metal doping" Nature, vol. 350, (1991), pp. 320–322.
Sijbesma, R. et al., "Synthesis of a Fullerene Derivative for the Inhibition of HIV Enzymes" J. Am. Chem. Soc. 1993, vol. 115, pp. 6510–6512.
Suzuki, T. et al., "Dihydrofulleroid $H_2C_{61}$: Synthesis and Properties of the Parent Fulleroid" J. Am. Chem. Soc. 1992, vol. 114, pp. 7301–7302.
Leonard F. Lindoy, "$C_{60}$ Chemistry Expands", Nature, vol. 357, 11 Jun. 1992, pp. 443–444.
Rudy M. Baum, "Systematic Chemistry of $C_{60}$ Beginning to Emerge", C&EN San Francisco, Dec. 16, 1991, pp. 17–20.
F. Wudl et al., "Survey of Chemical Reactivity of $C_{60}$ Electrophile and Dieno—Polarophile Par Excellence", American Chemical Society, 1992, pp. 161–175.
Ram Seshadri et al., "Addition of Amines and Halogens to Fullerenes $C_{60}$ and $C_{70}$", Tetrahedron Letters, vol. 33, No. 15, 1992, pp. 2069–2070.
Andreas Hirsh et al., "Titration of $C_{60}$: A method For the Synthesis of Organofullerenes", Angew. Chem. Int. Ed. Engl., 31 (1992) No. 6, pp. 766–768 (English) and 808–10 (German).

Primary Examiner—Philip I. Datlow
Attorney, Agent, or Firm—Curtis, Morris & Safford, P.C.

[57] ABSTRACT

The invention relates to an addition compound which is obtainable by reaction of a diamine of the formula I,

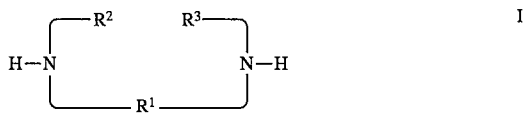

where $R^1$ is $(C_2–C_4)$-alkylene or 1,2- or 1,3-cyclo-$(C_3–C_7)$-alkylene and $R^2$ and $R^3$, which are identical or different, are $(C_1–C_3)$-alkyl or hydrogen or $R^2$ and $R^3$ together are $(C_2–C_4)$-alkylene, with fullerenes $C_{60}$ and/or $C_{70}$. The fullerene derivatives are useful as electrically conducting materials.

20 Claims, 29 Drawing Sheets

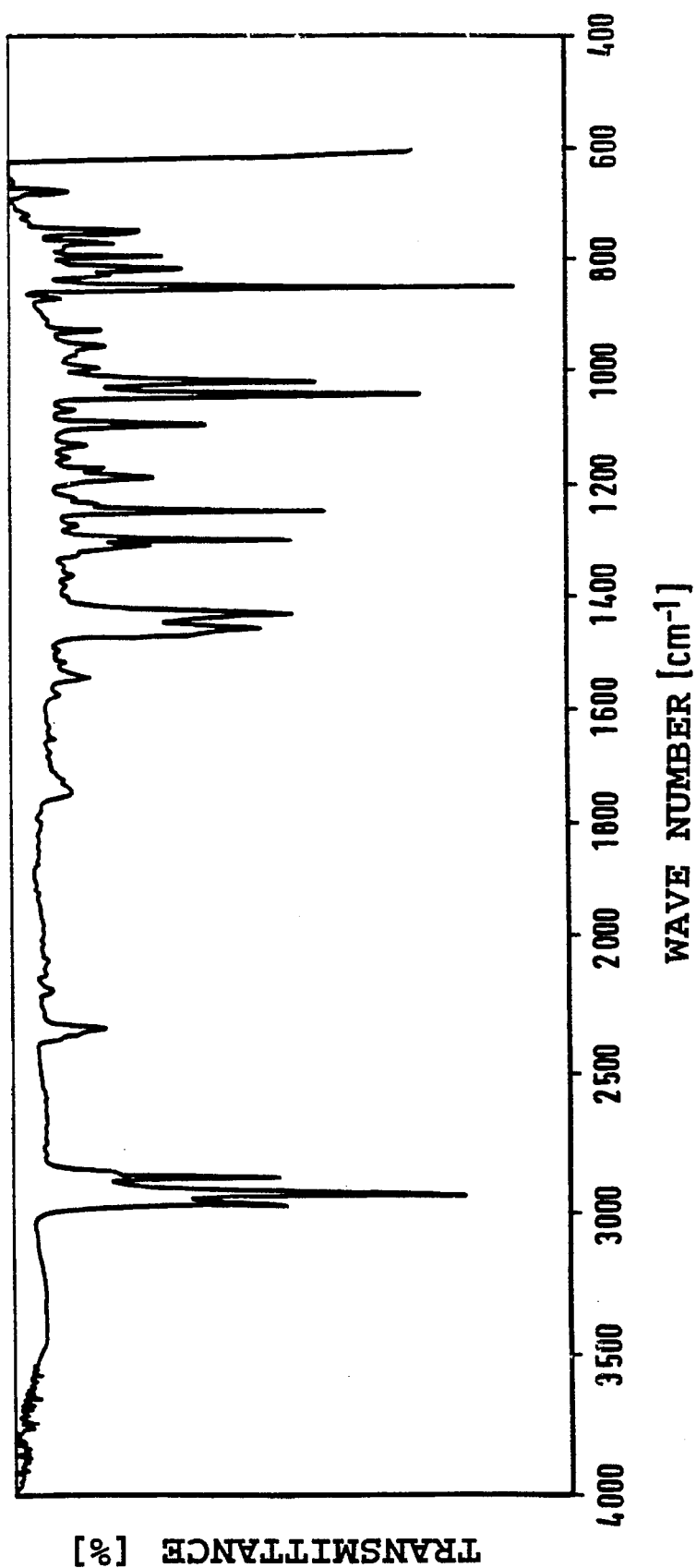
Fig. 1  IR spectrum  Monoaddition compound (Addition compound no. 1)

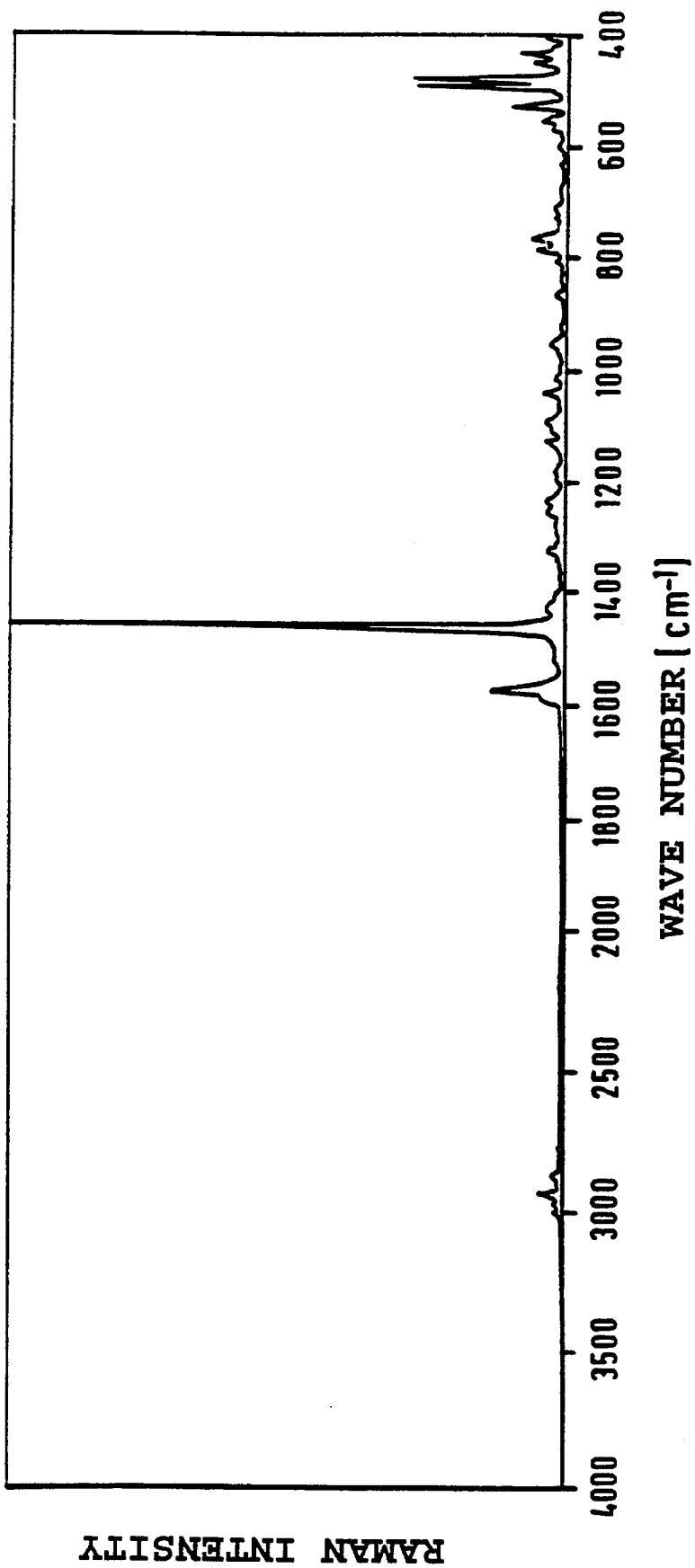
Fig. 2 Raman spectrum Monoaddition compound (Addition compound no. 1)

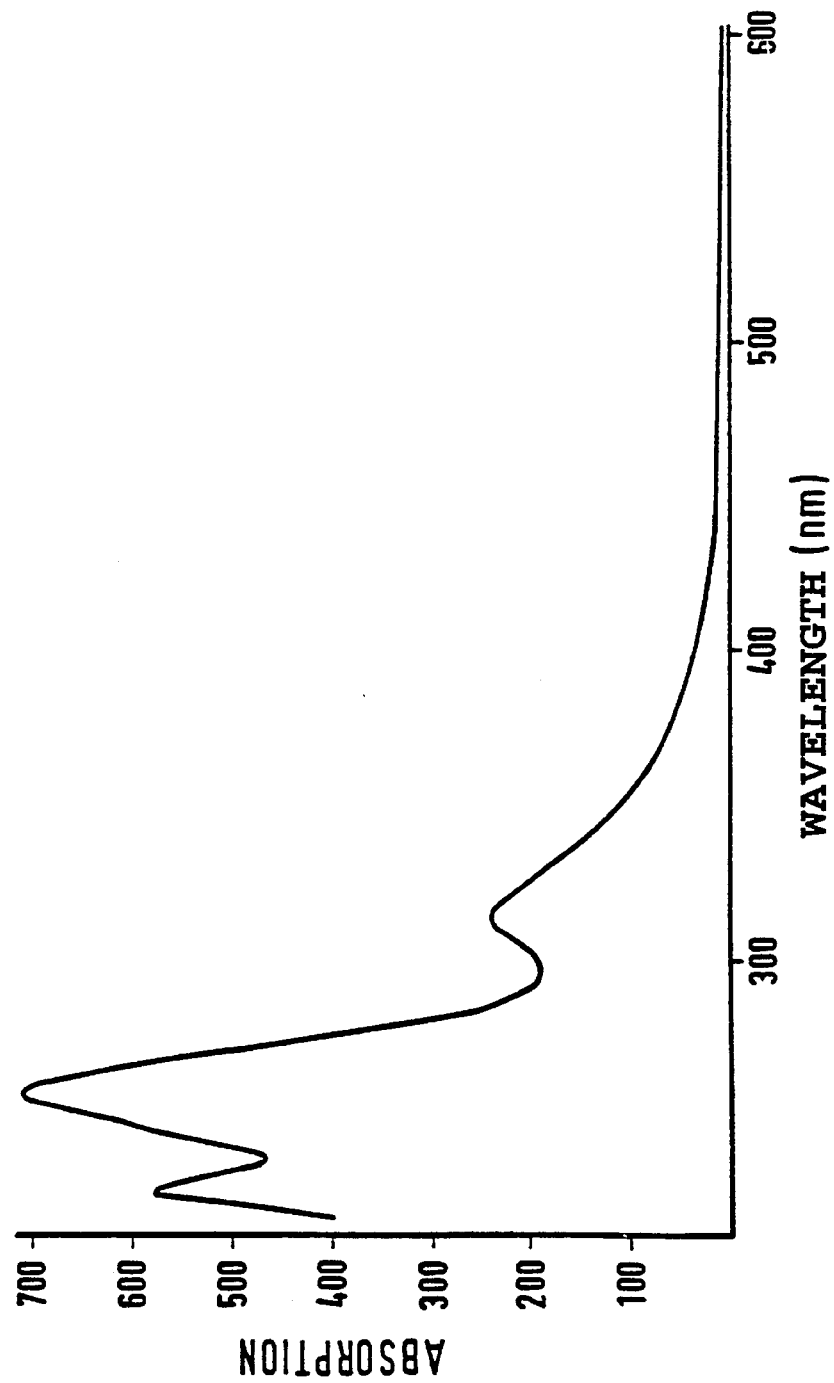
Fig. 3  UV spectrum
Monoaddition compound
(Addition compound no. 1)

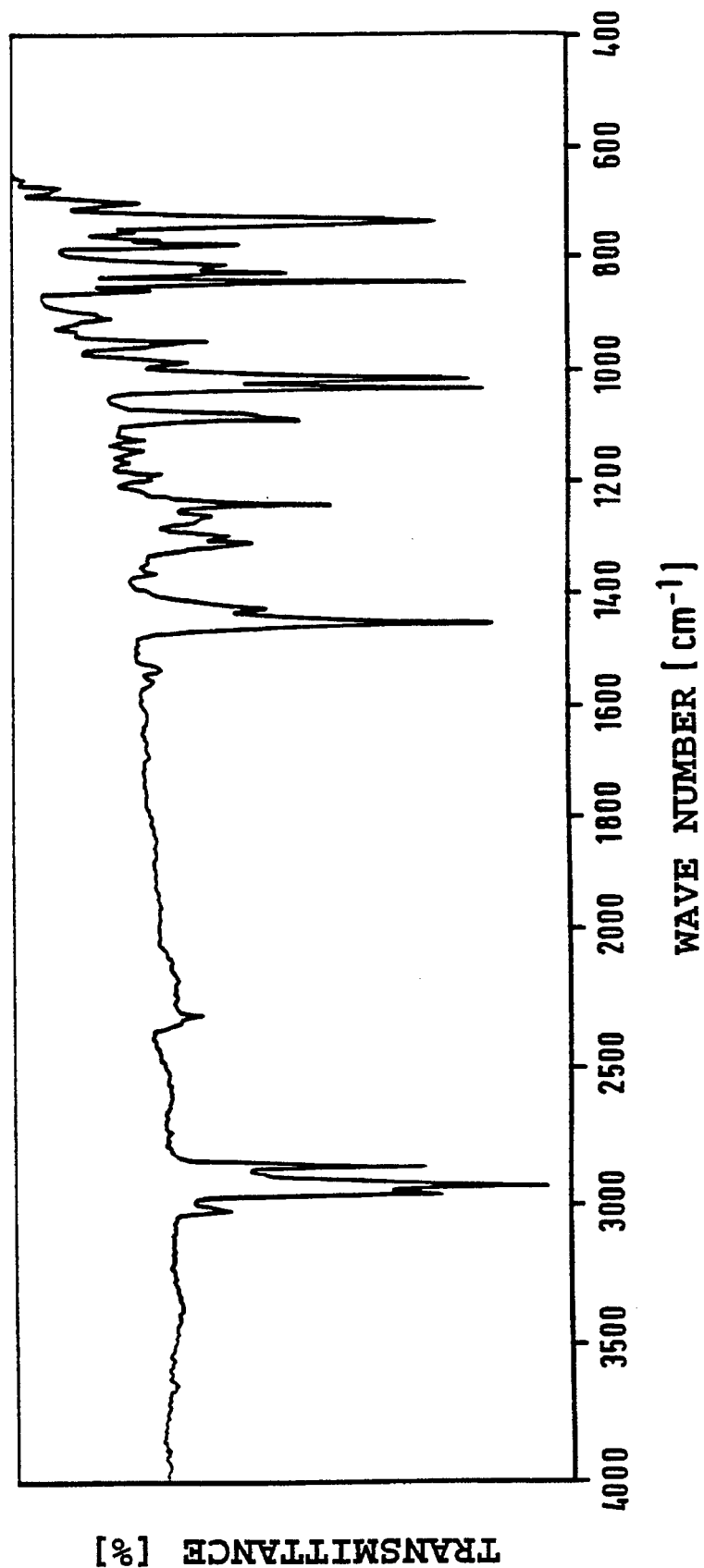

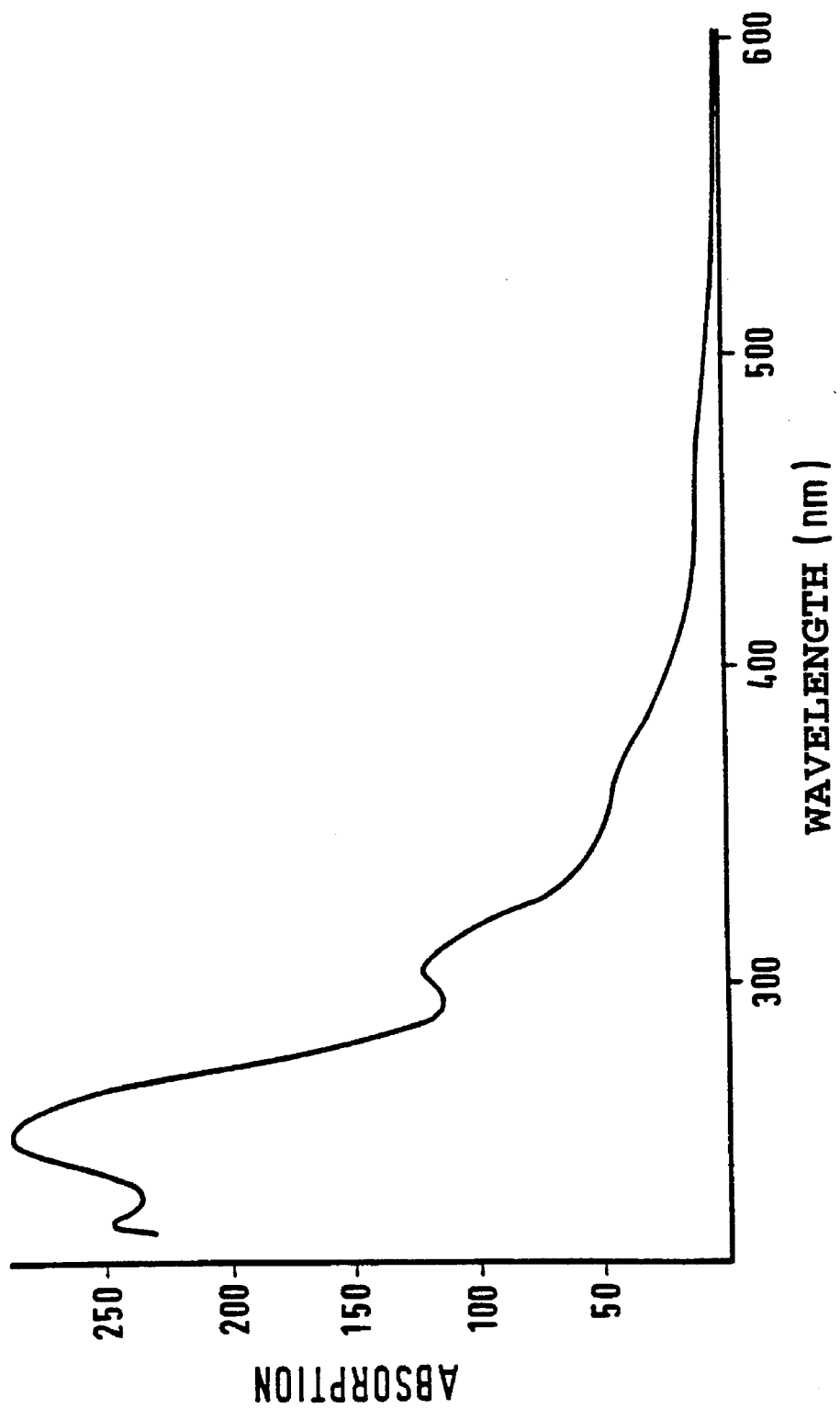
Fig. 5  UV spectrum
Addition compound no. 2

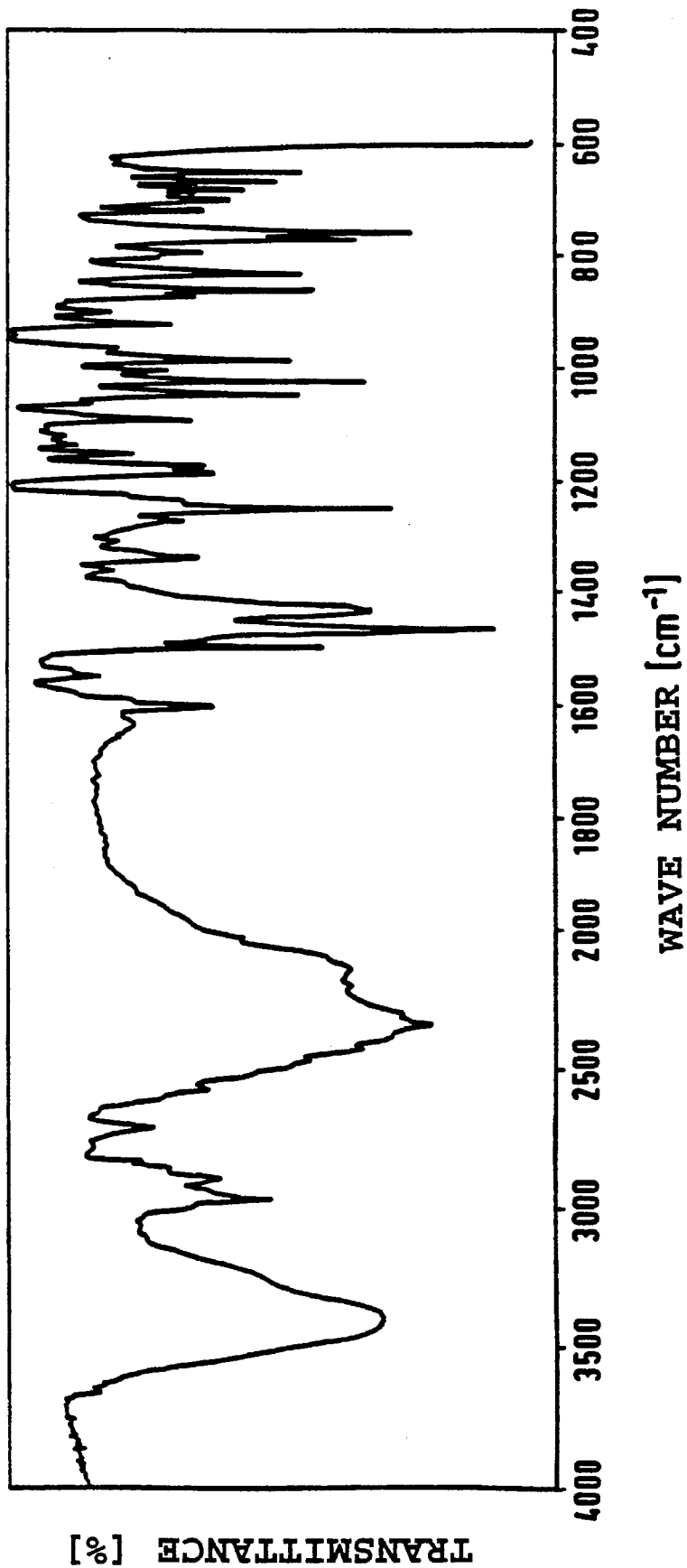
Fig. 6  IR spectrum
Hydrochloride of the monoaddition compound
(Addition compound no. 1)

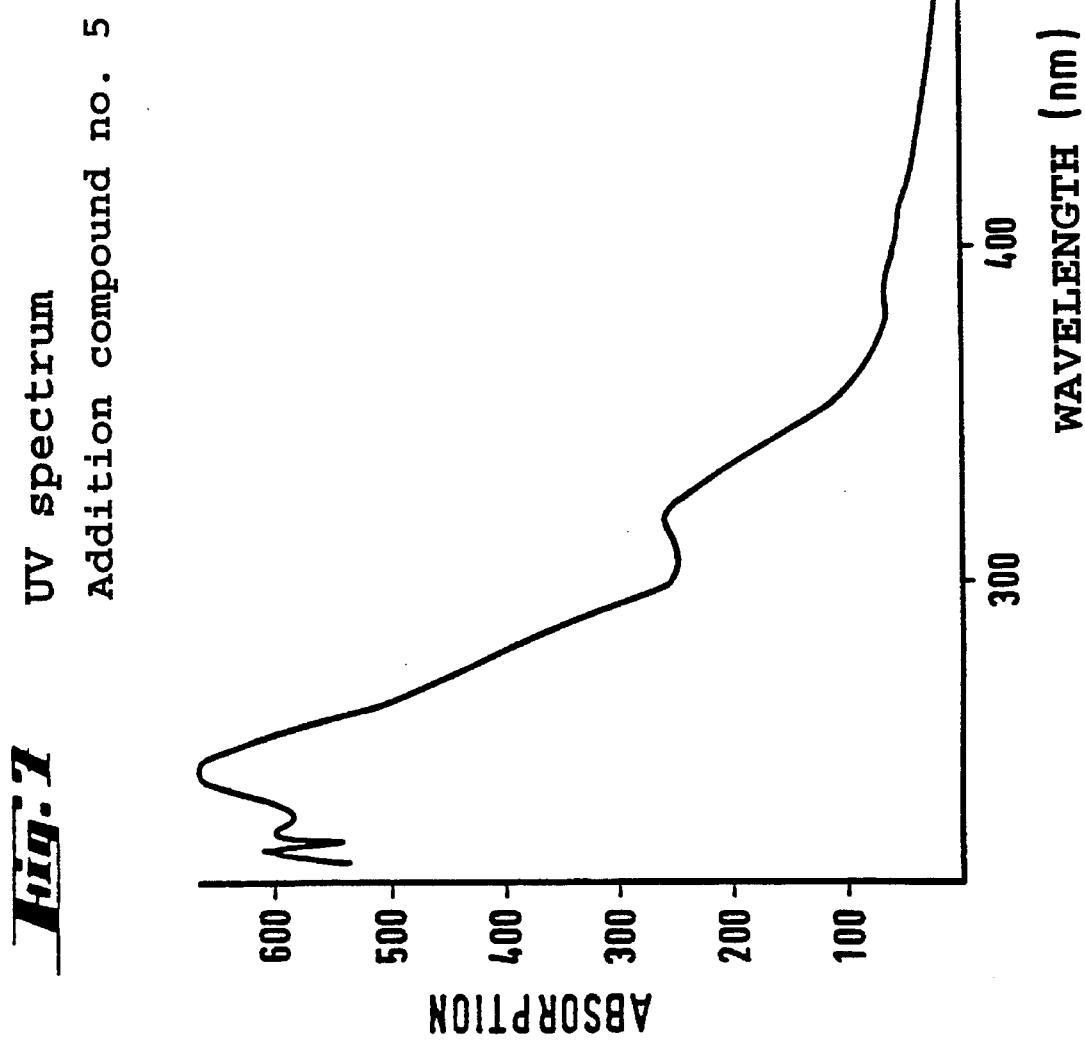
Fig. 7  UV spectrum
Addition compound no. 5

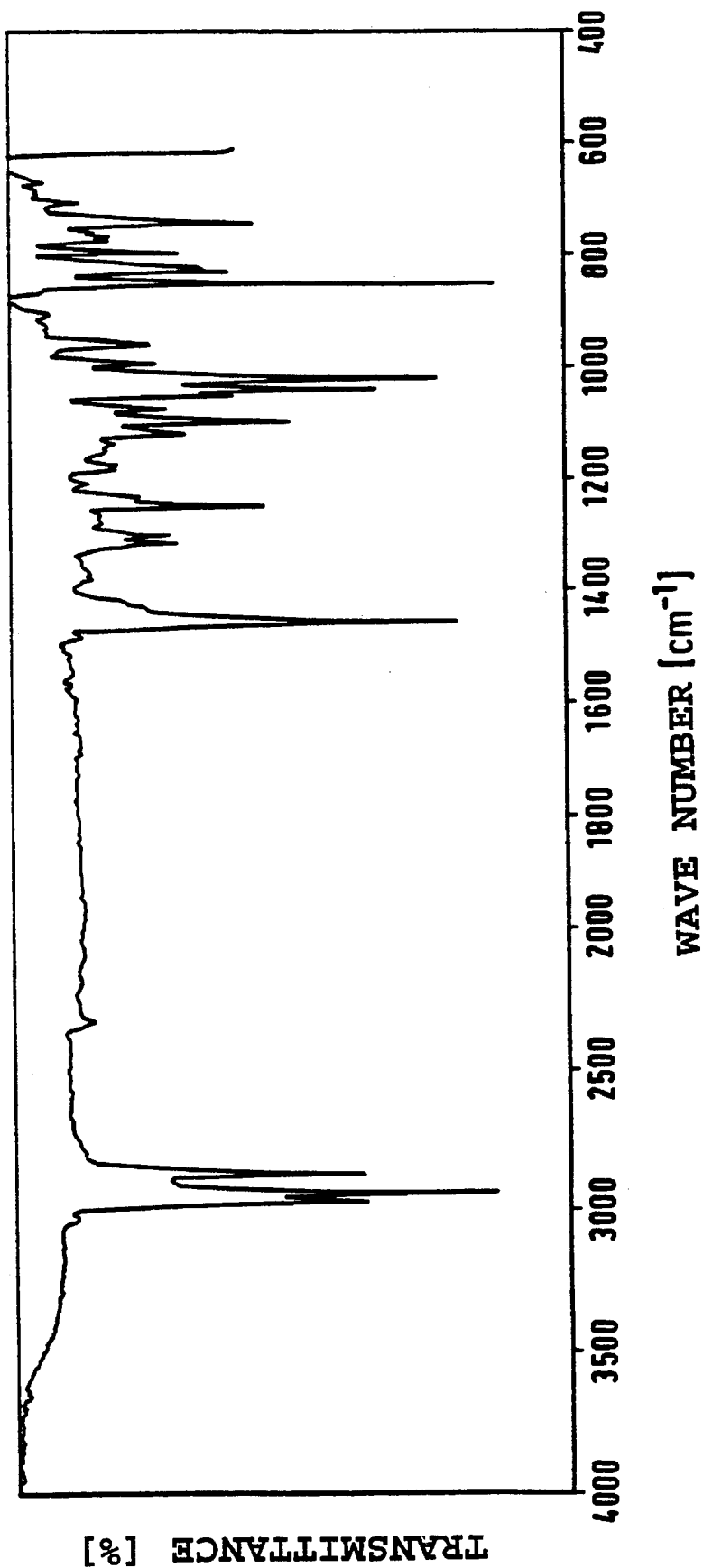

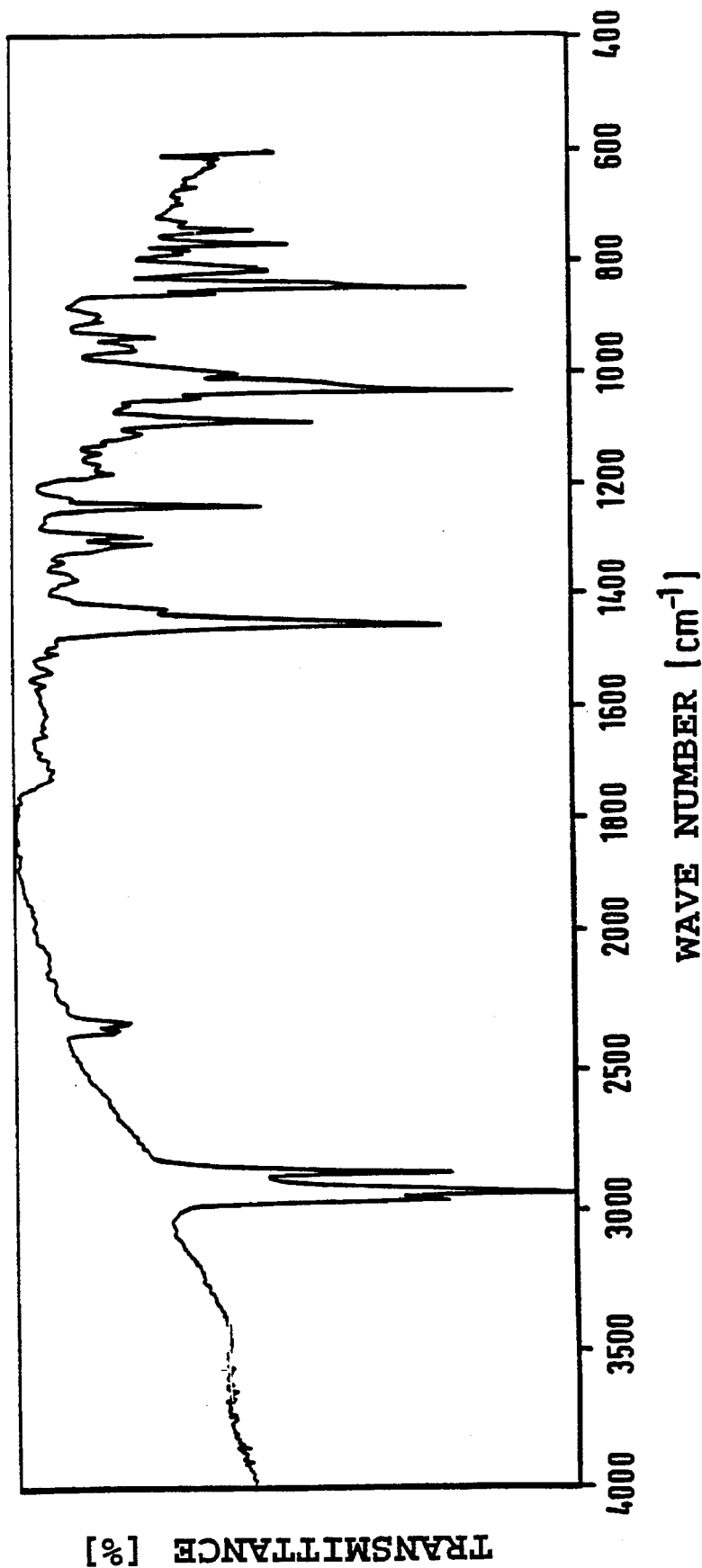
Fig. 9   IR spectrum   Diaddition compound no. 3

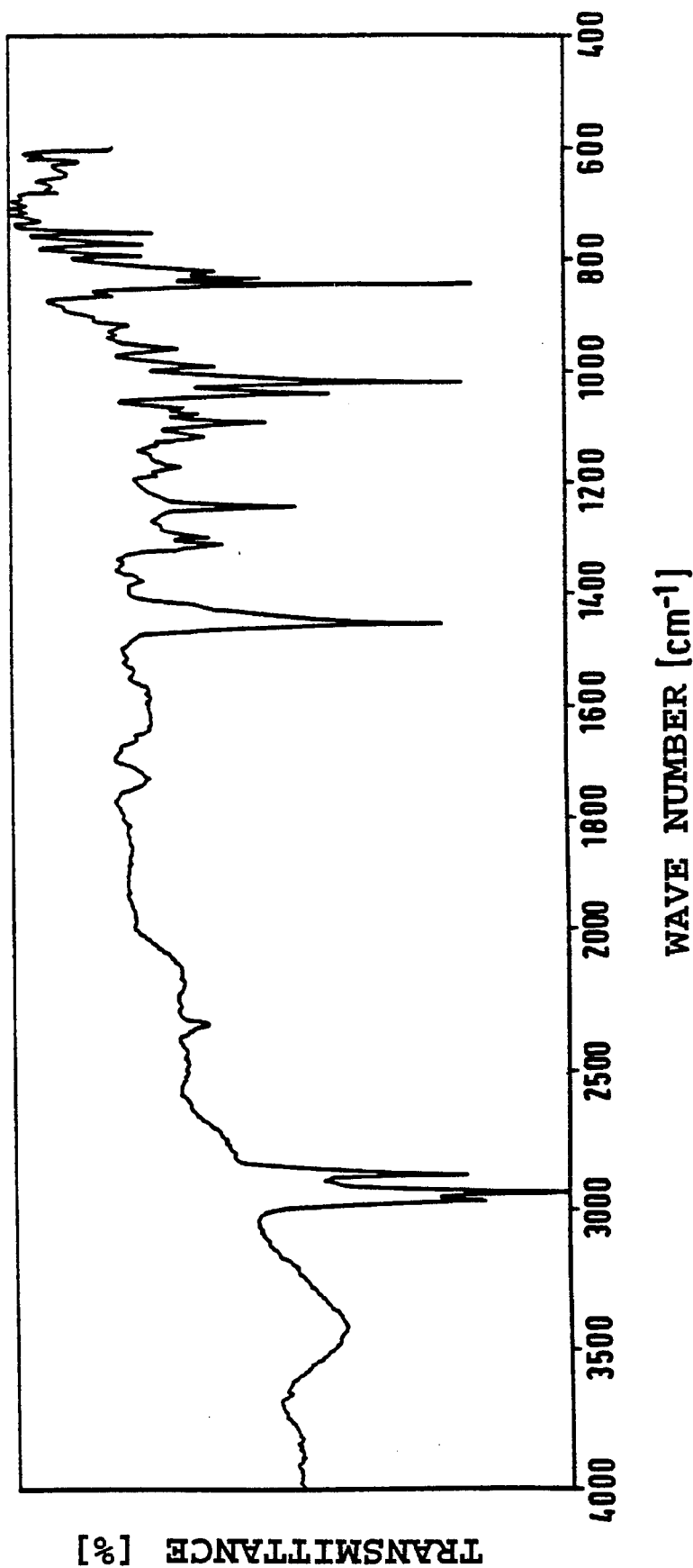
Fig. 10  IR spectrum  Diaddition compound no. 3a

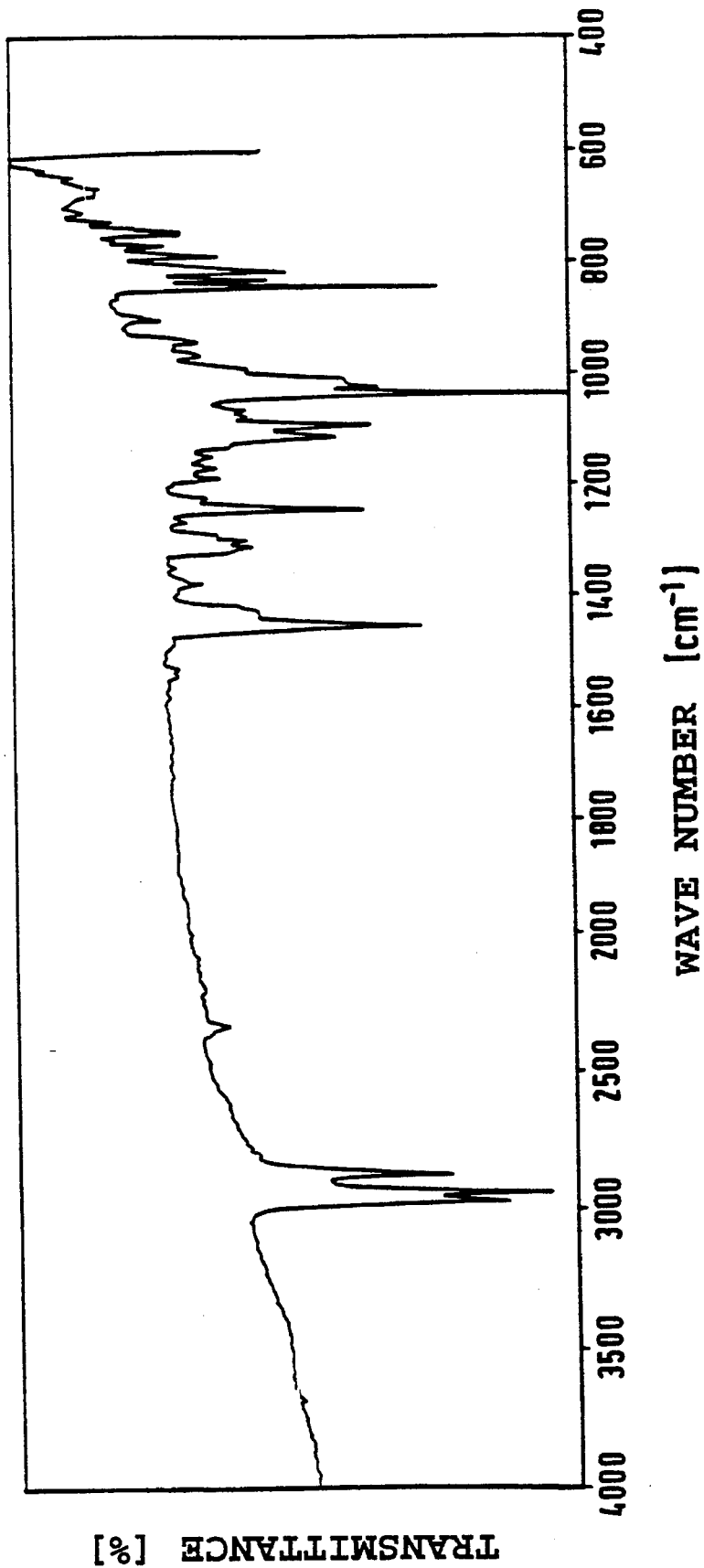
Fig. 11  IR spectrum  Diaddition compound no. 4

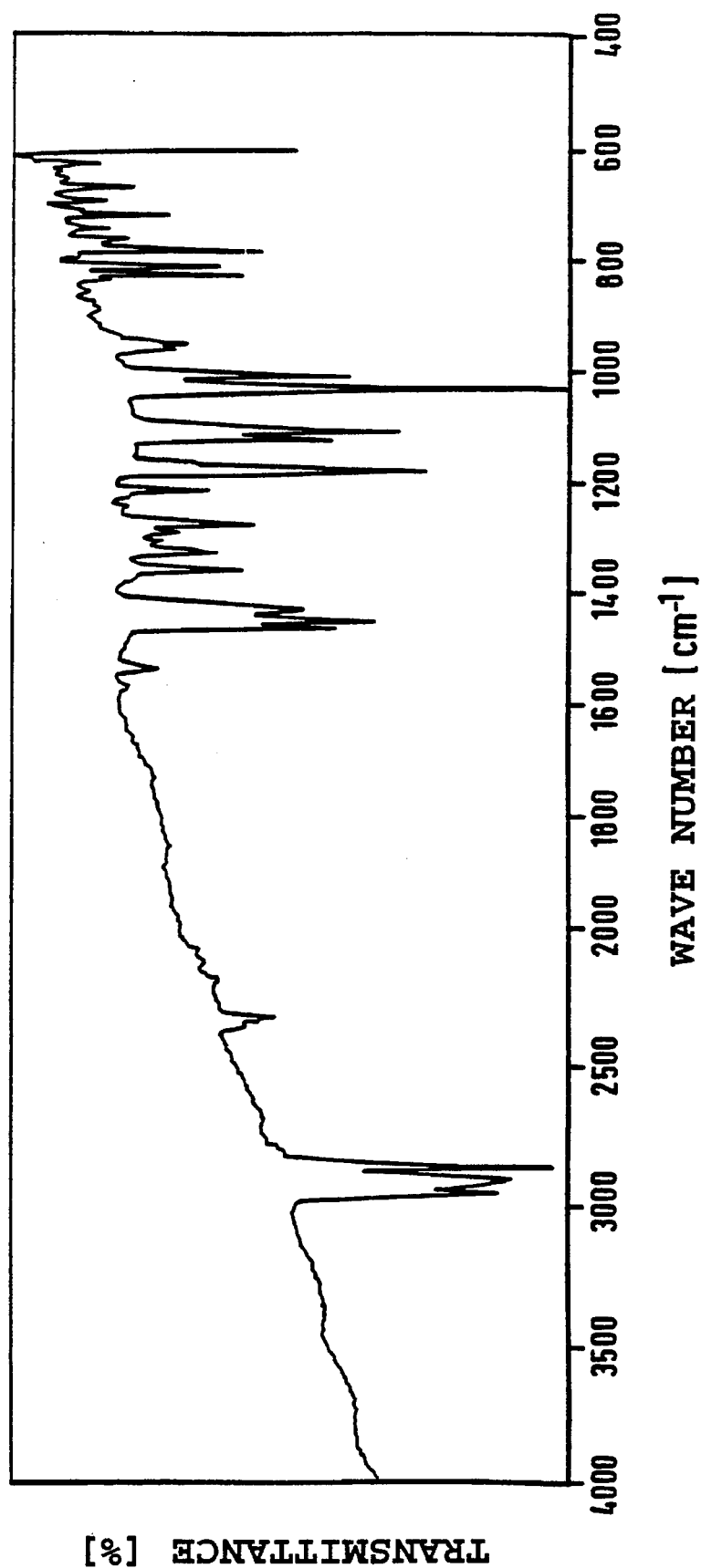

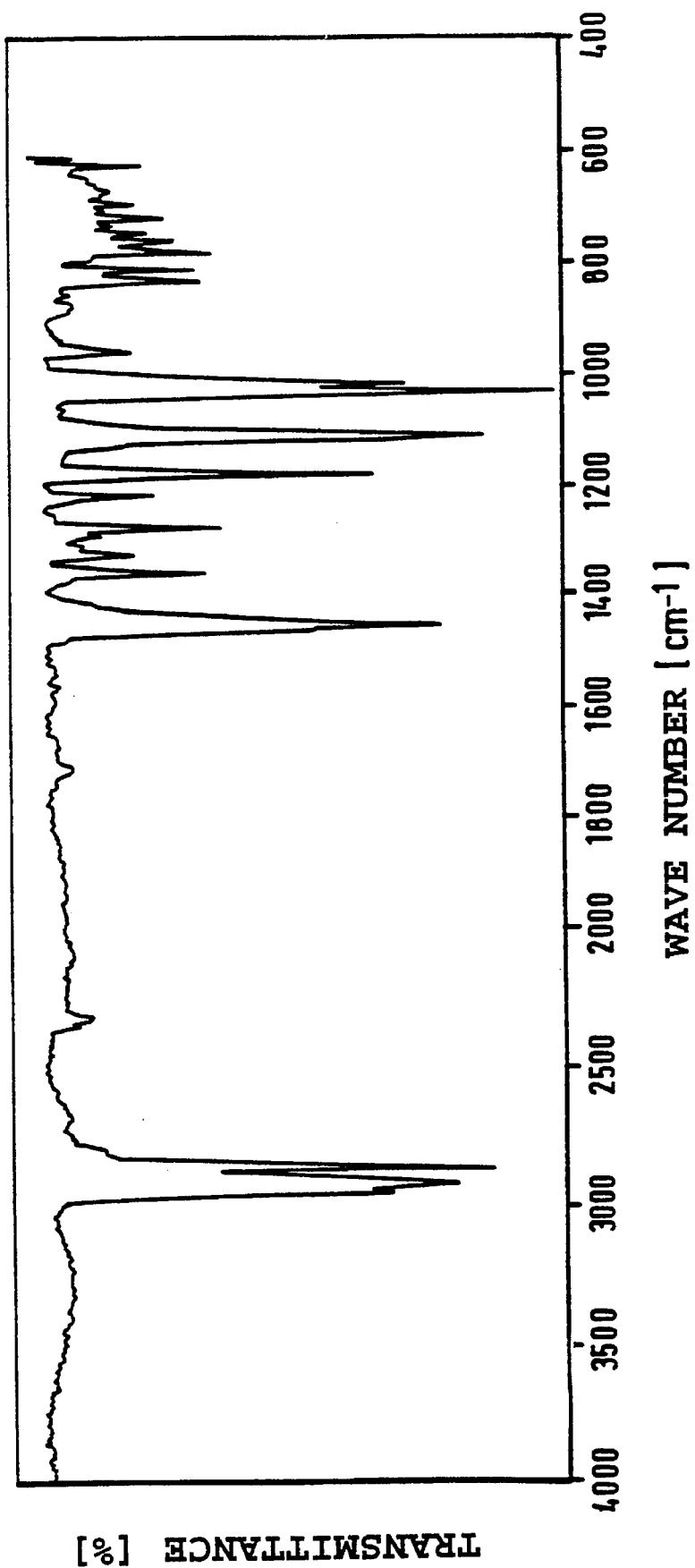
Fig. 13  IR spectrum  Diaddition compound no. 11

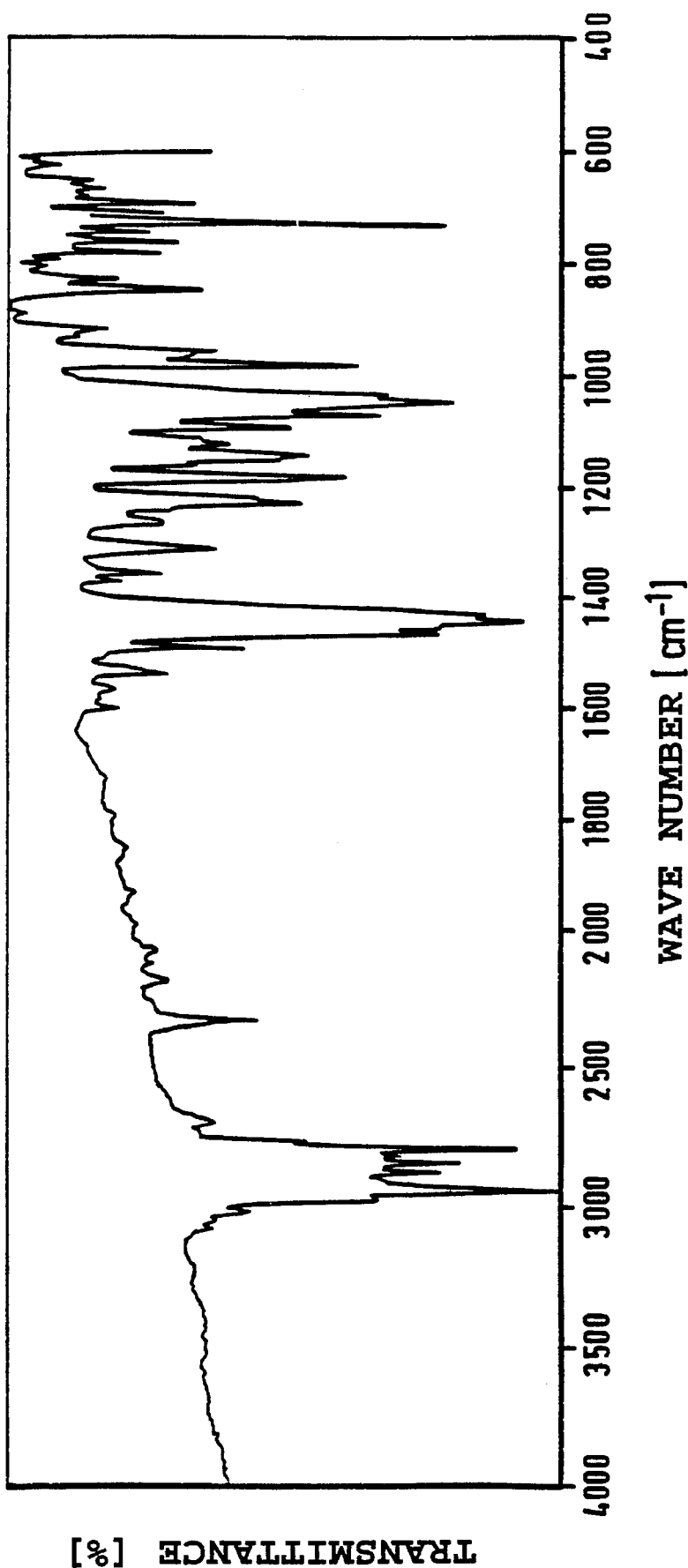
Fig. 14.   IR spectrum
Monoaddition compound no. 12

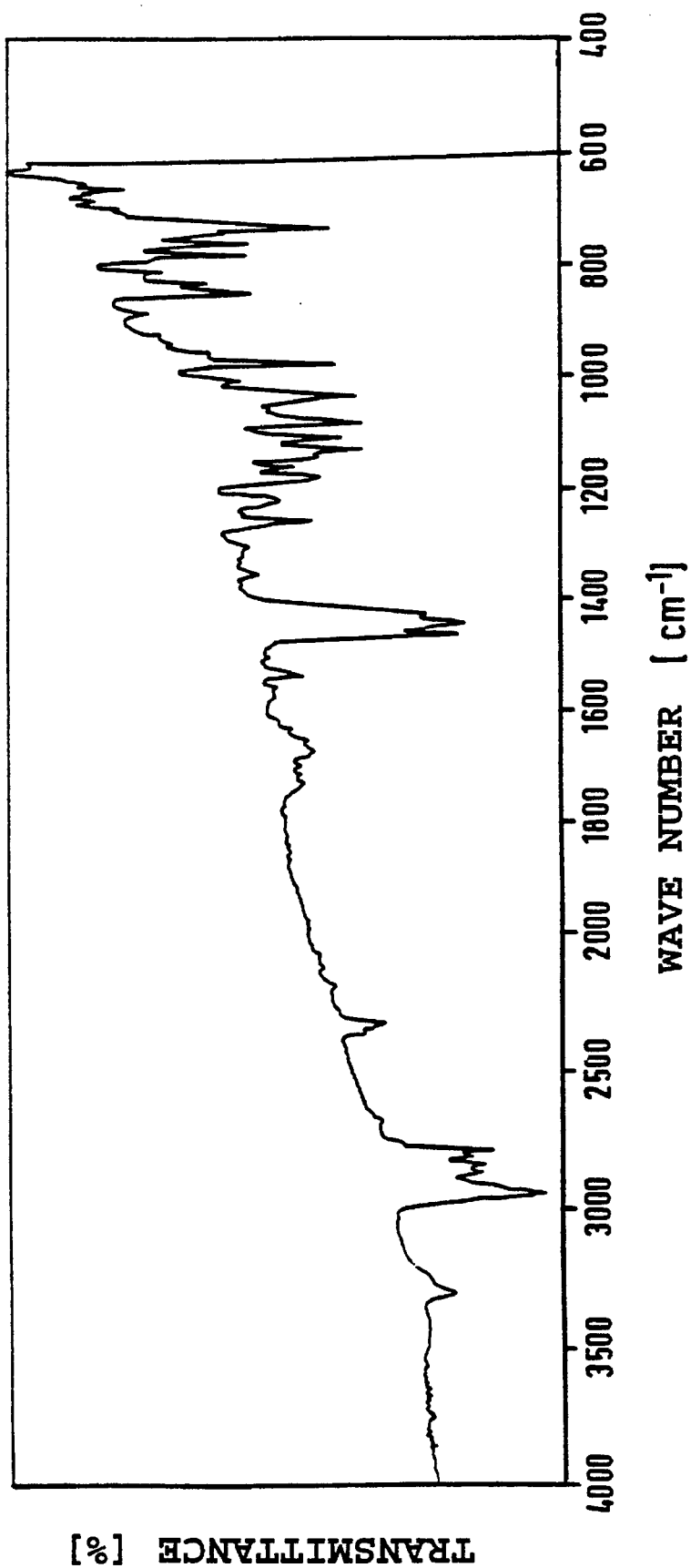
Fig. 15  IR spectrum  Diaddition compound no. 13a

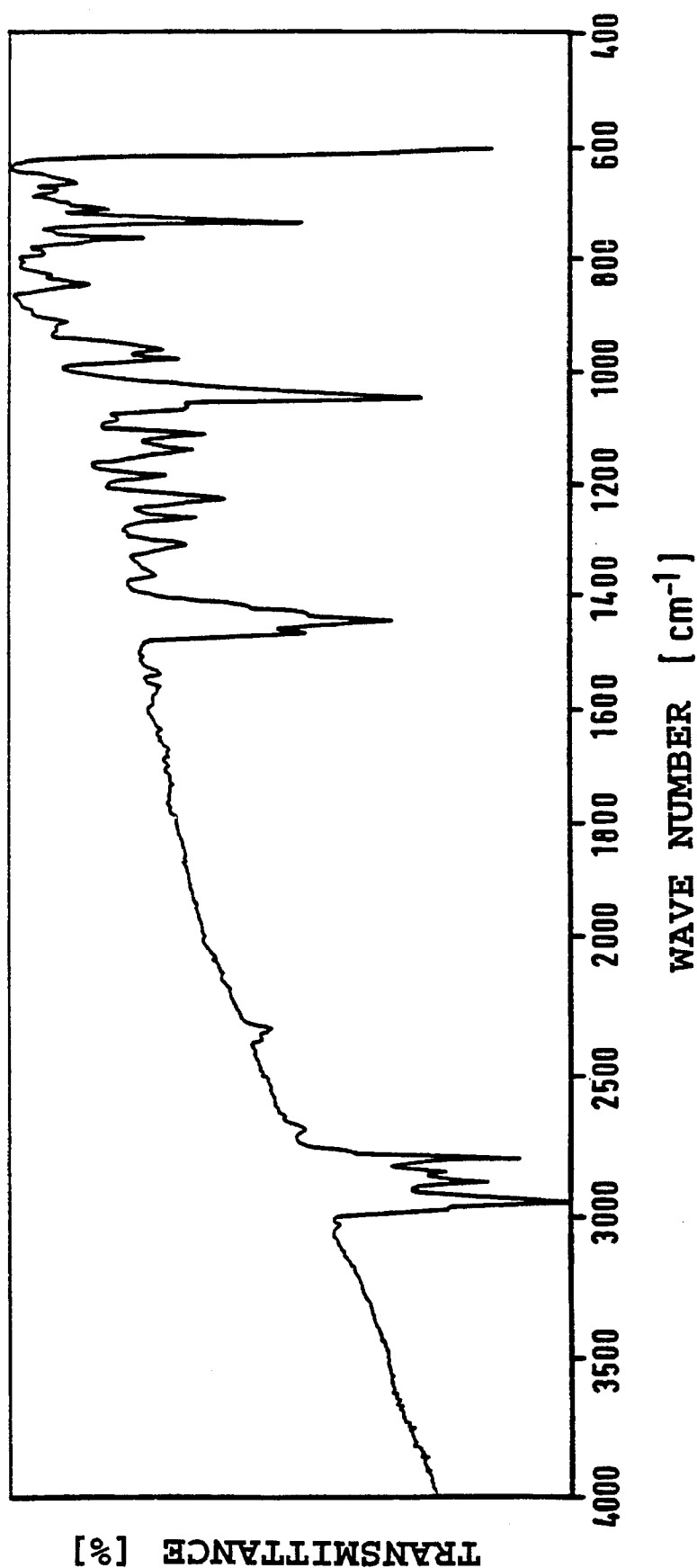
Fig. 16  IR spectrum  Diaddition compound no. 13b

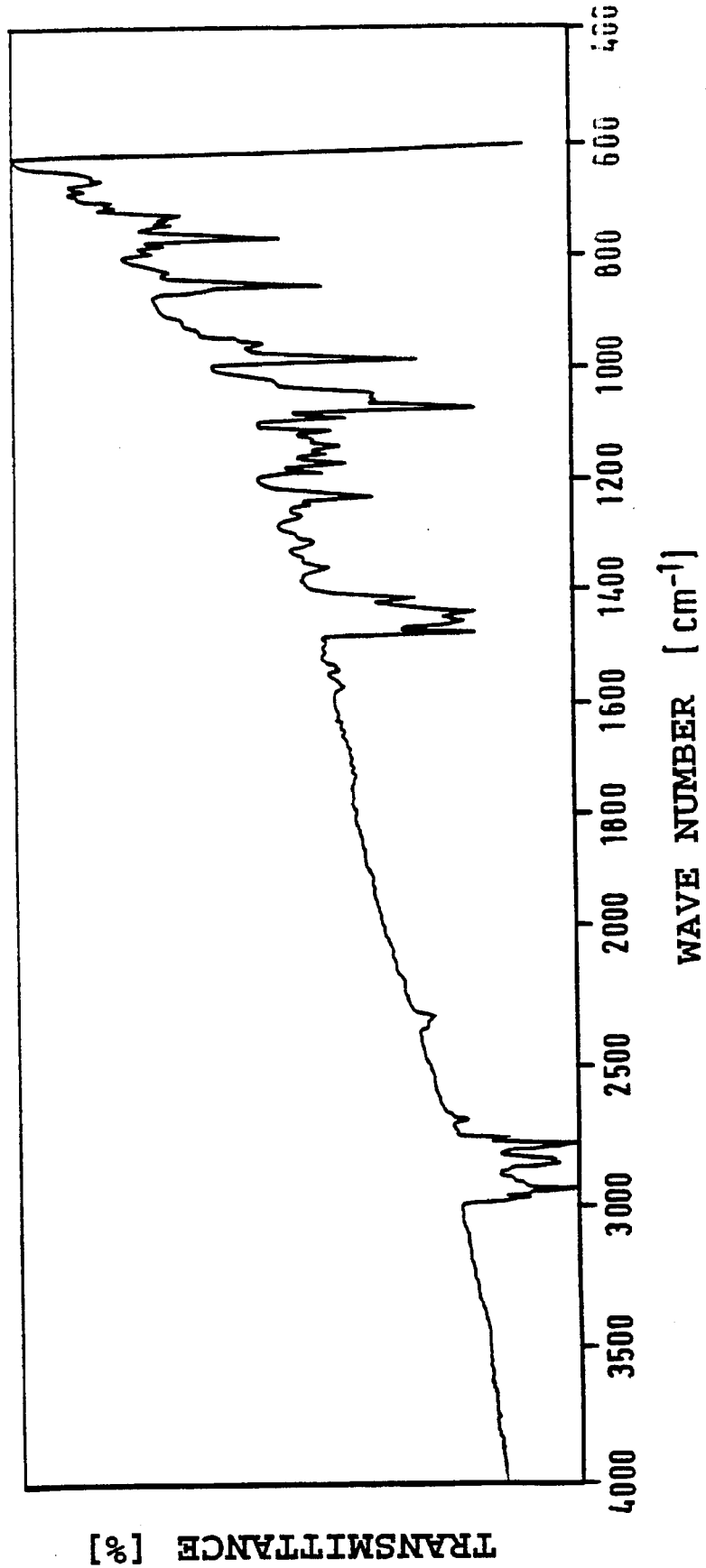
Fig. 17  IR spectrum  Diaddition compound no. 13

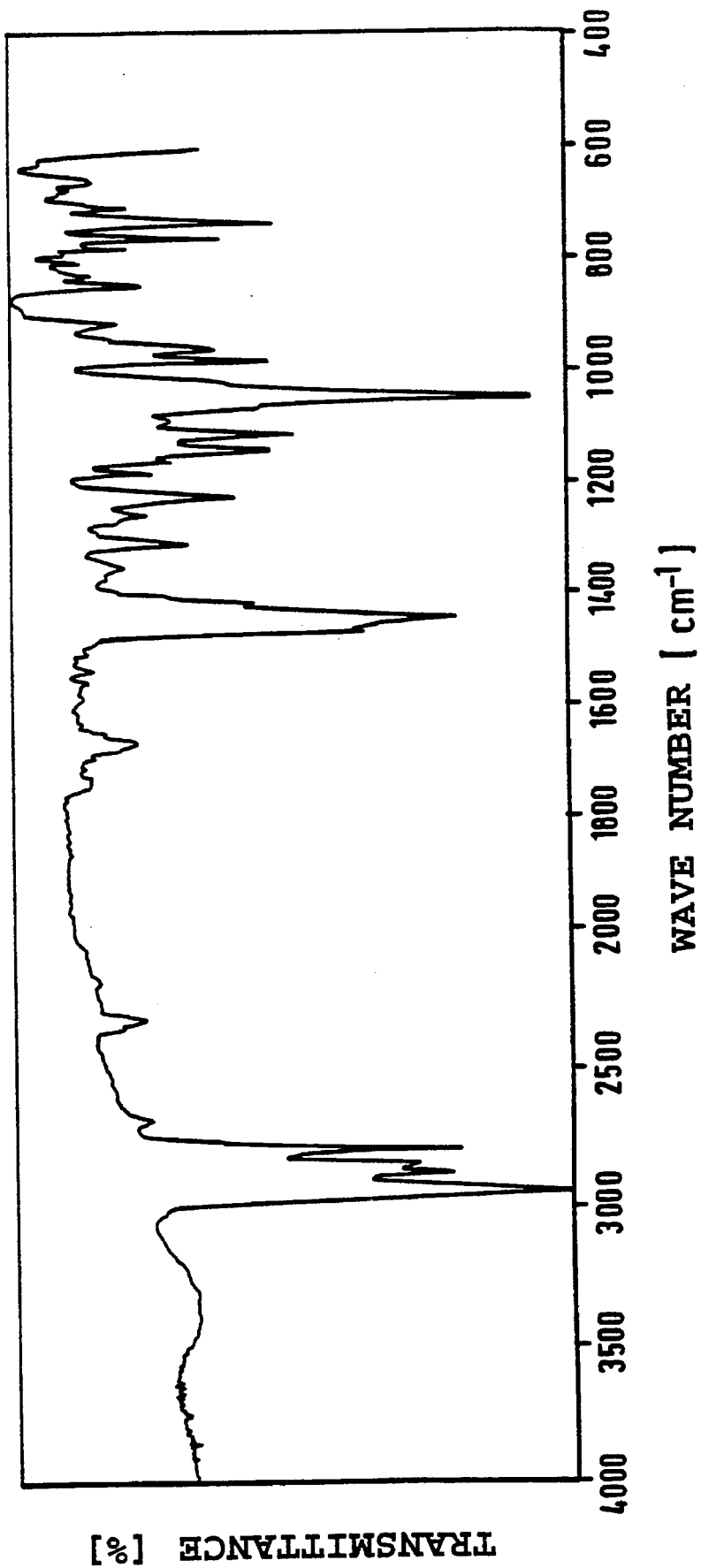
Fig. 18  IR spectrum  Diaddition compound no. 13c

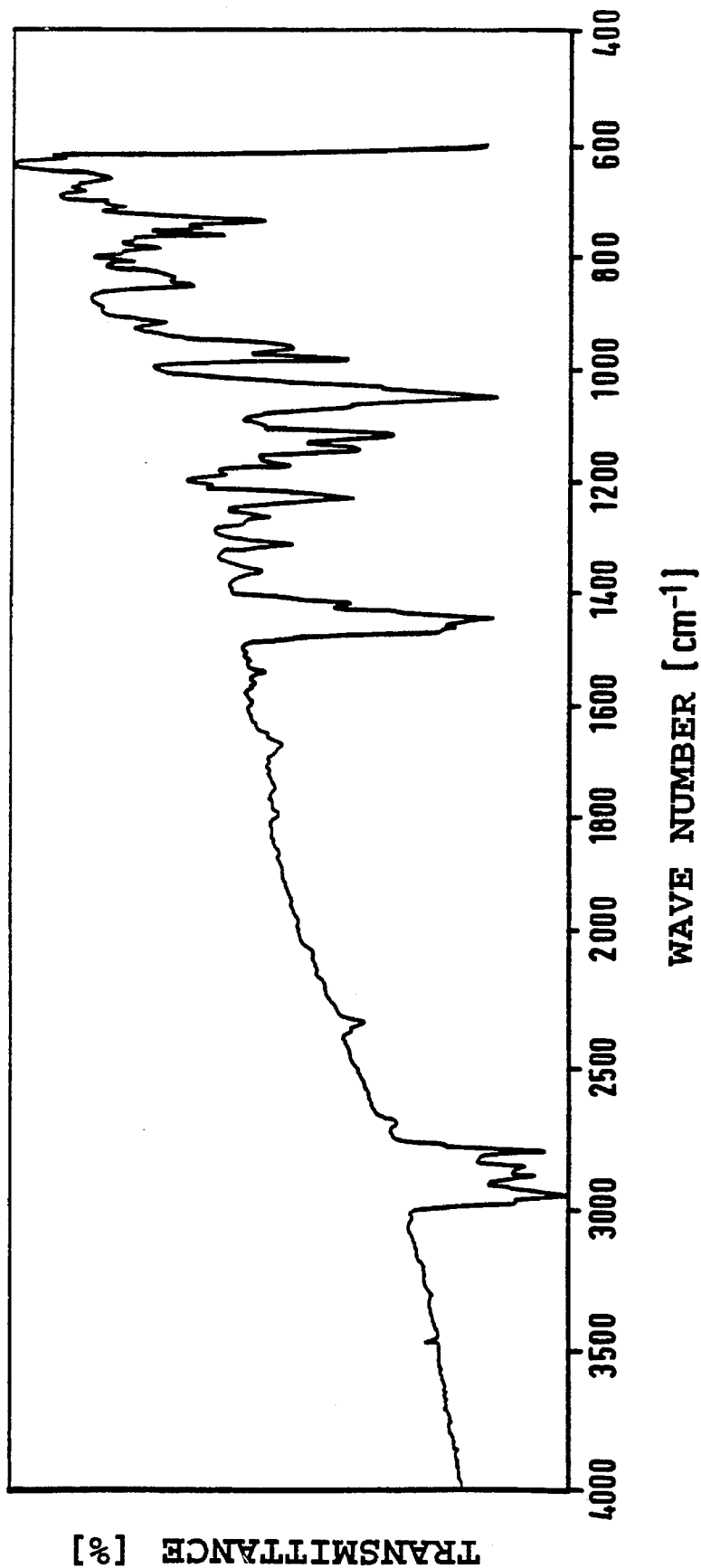
Fig. 19 IR spectrum Diaddition compound no. 14

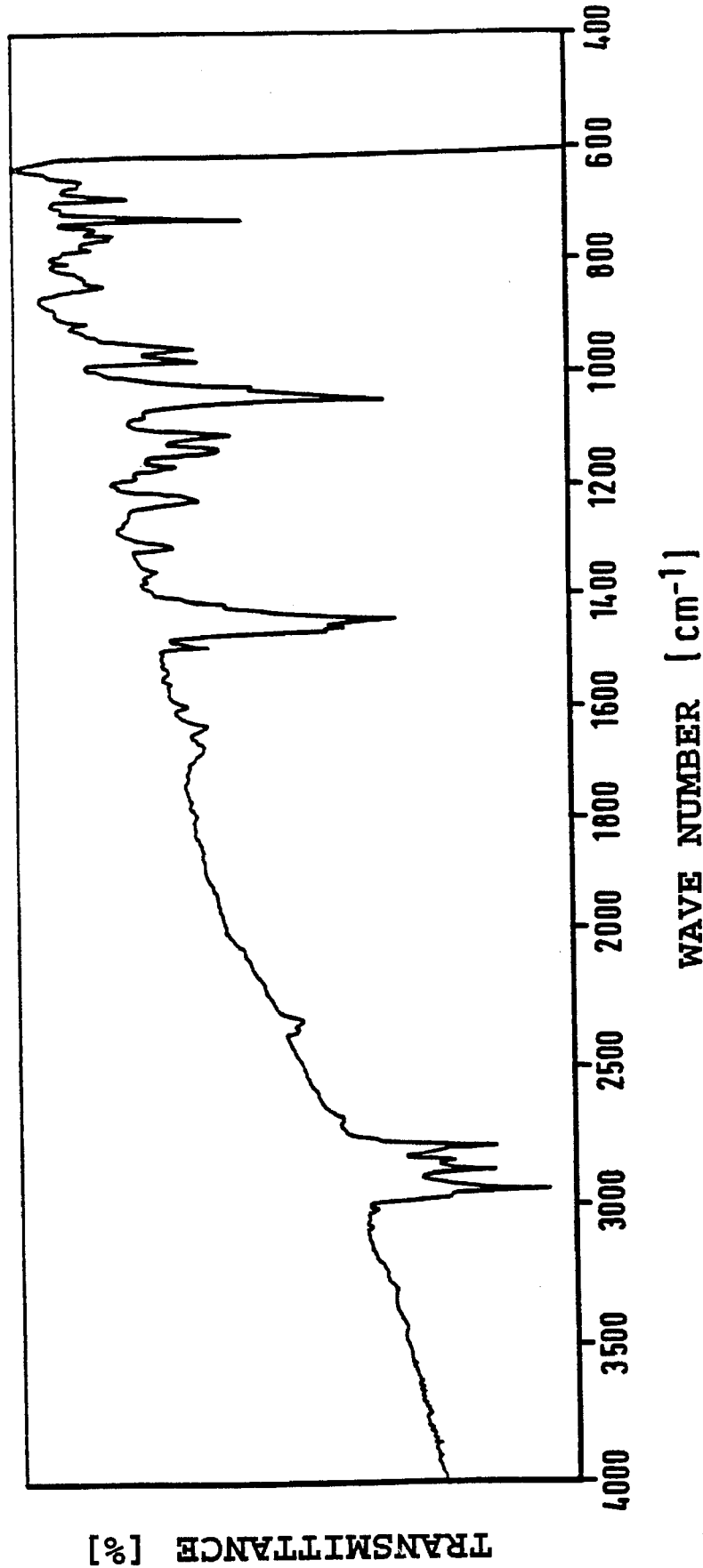
Fig. 20  IR spectrum
Diaddition compound no. 15

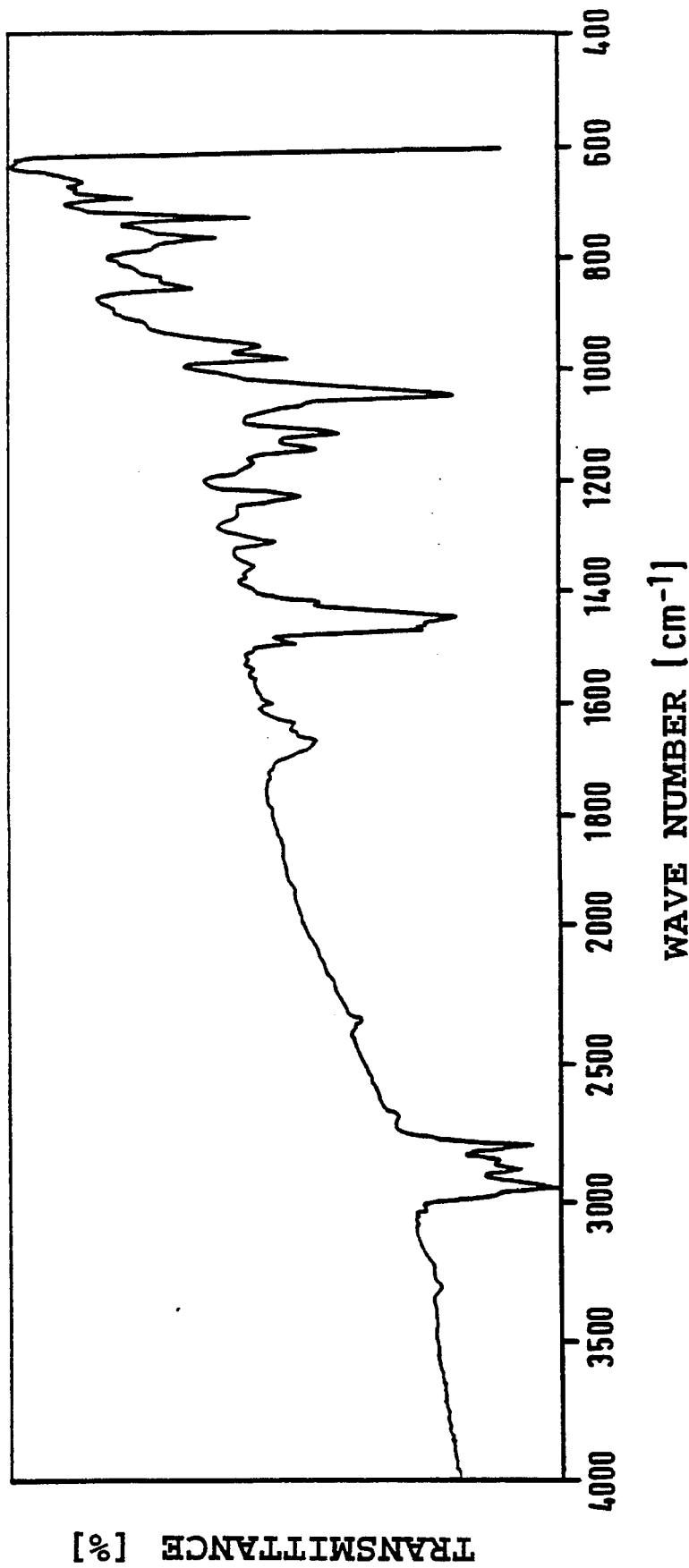
Fig. 21  IR spectrum  Diaddition compound no. 16

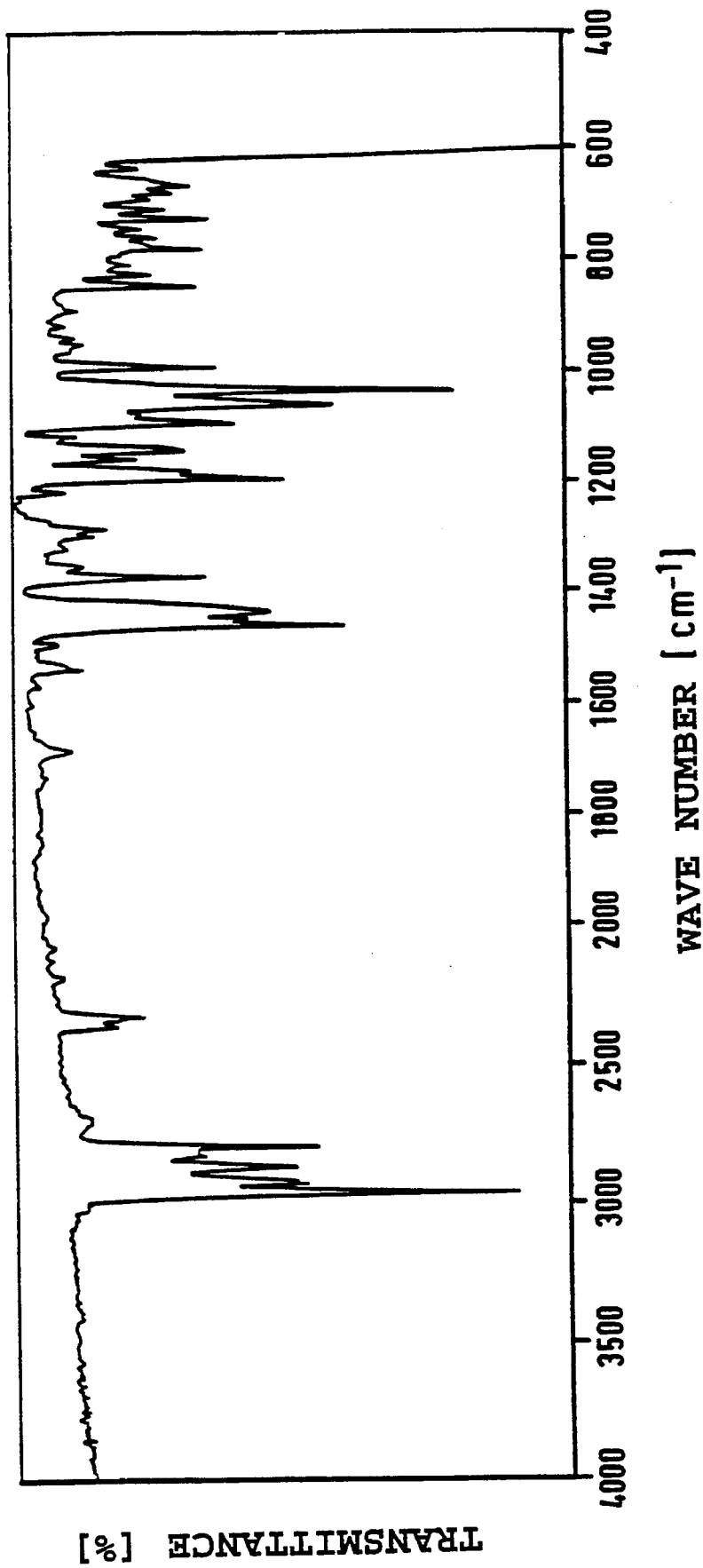
Fig. 22  IR spectrum
Monoaddition compound no. 17

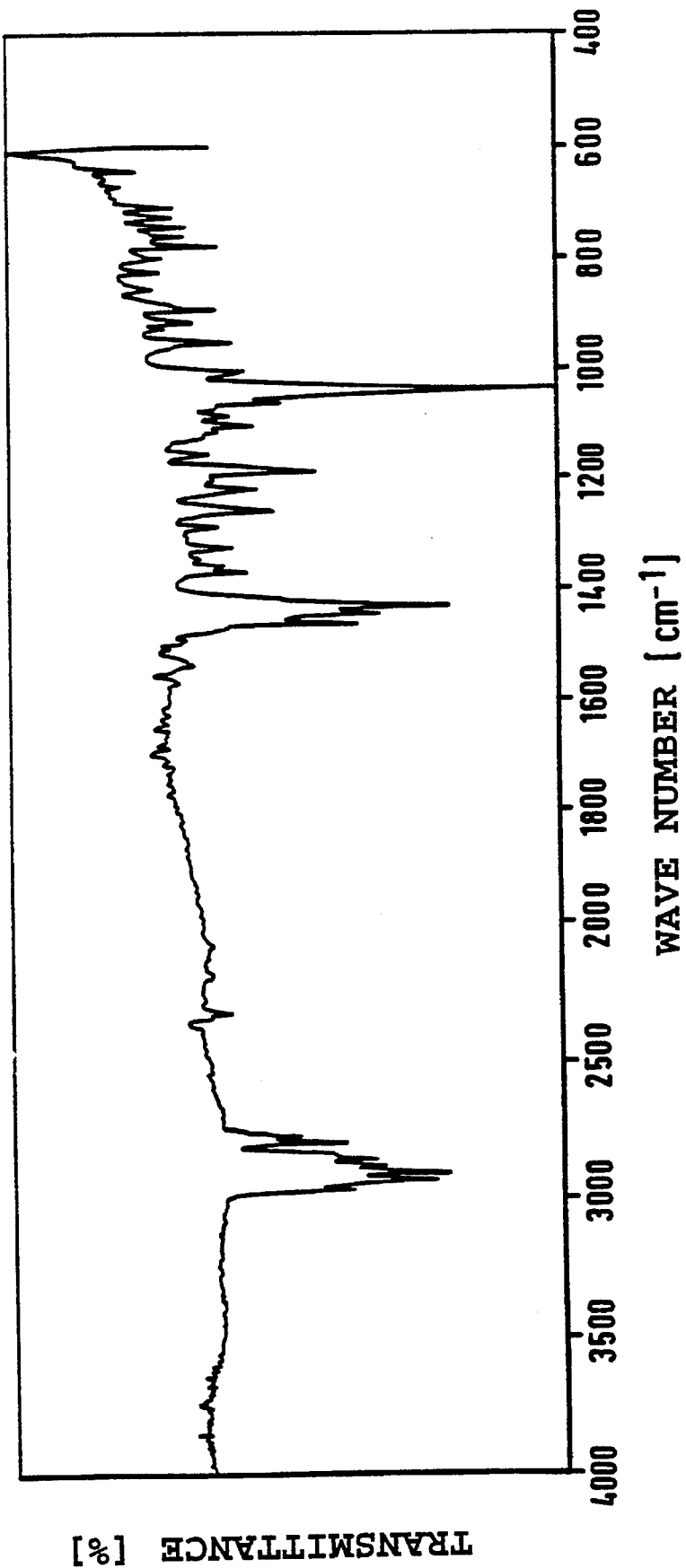
Fig. 23  IR spectrum
Monoaddition compound no. 18

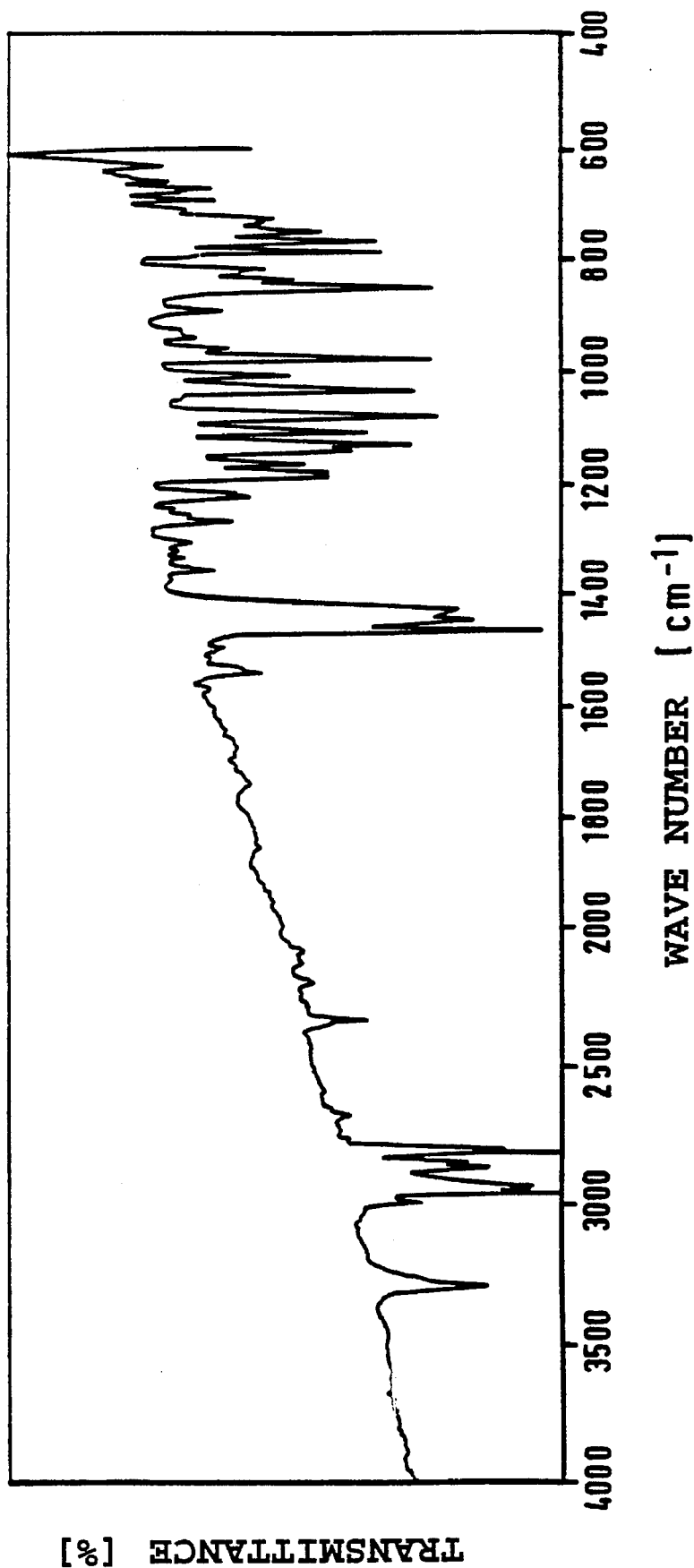
Fig. 24. IR spectrum Monoaddition compound no. 19

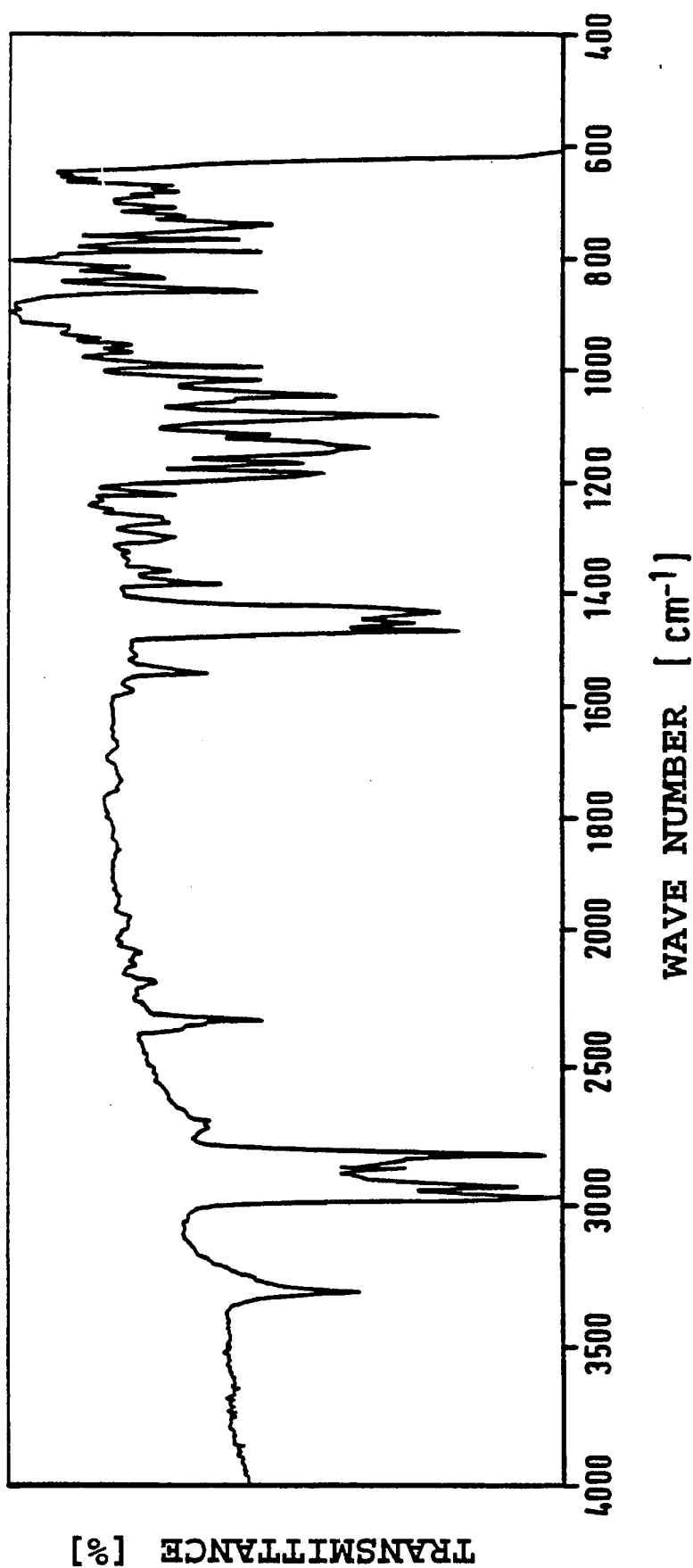
Fig. 25  IR spectrum
Monoaddition compound no. 20

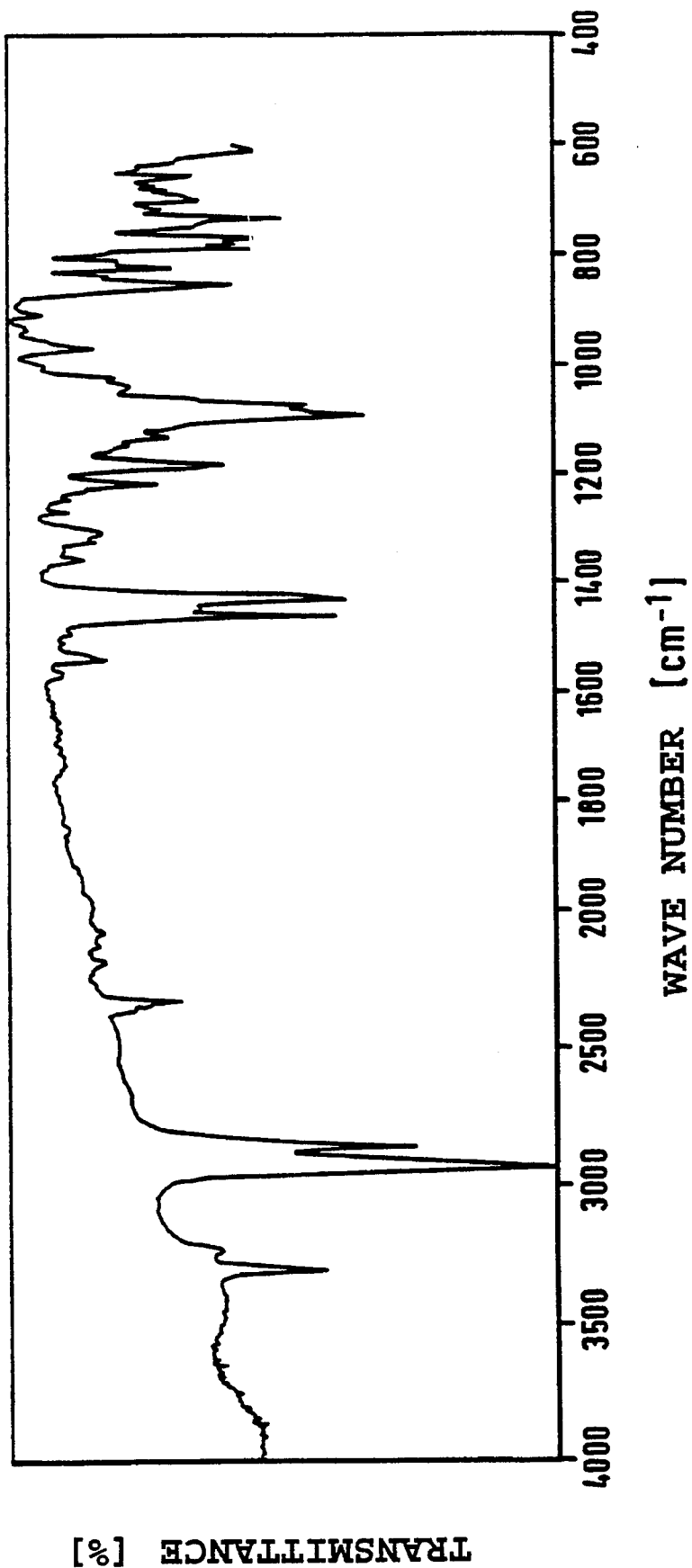

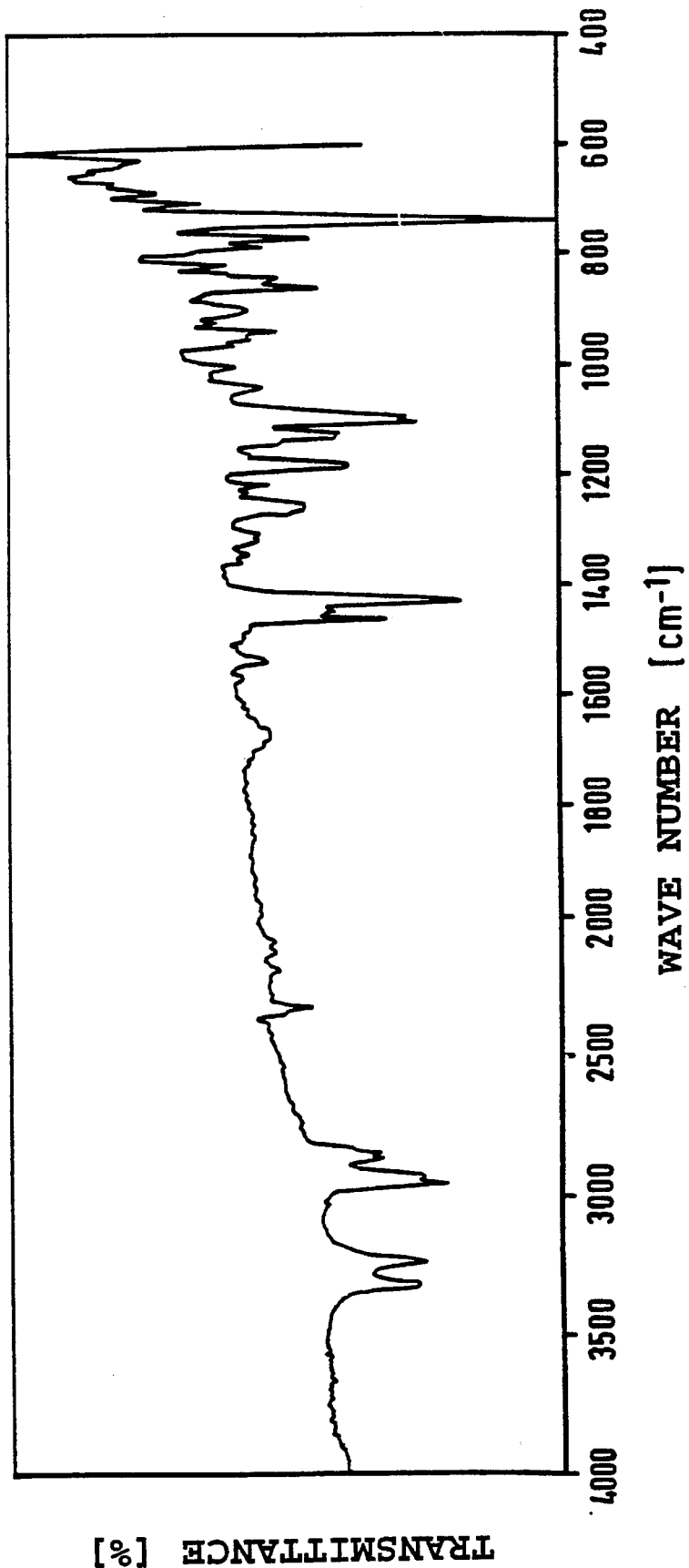
Fig. 27  IR spectrum  Monoaddition compound no. 22

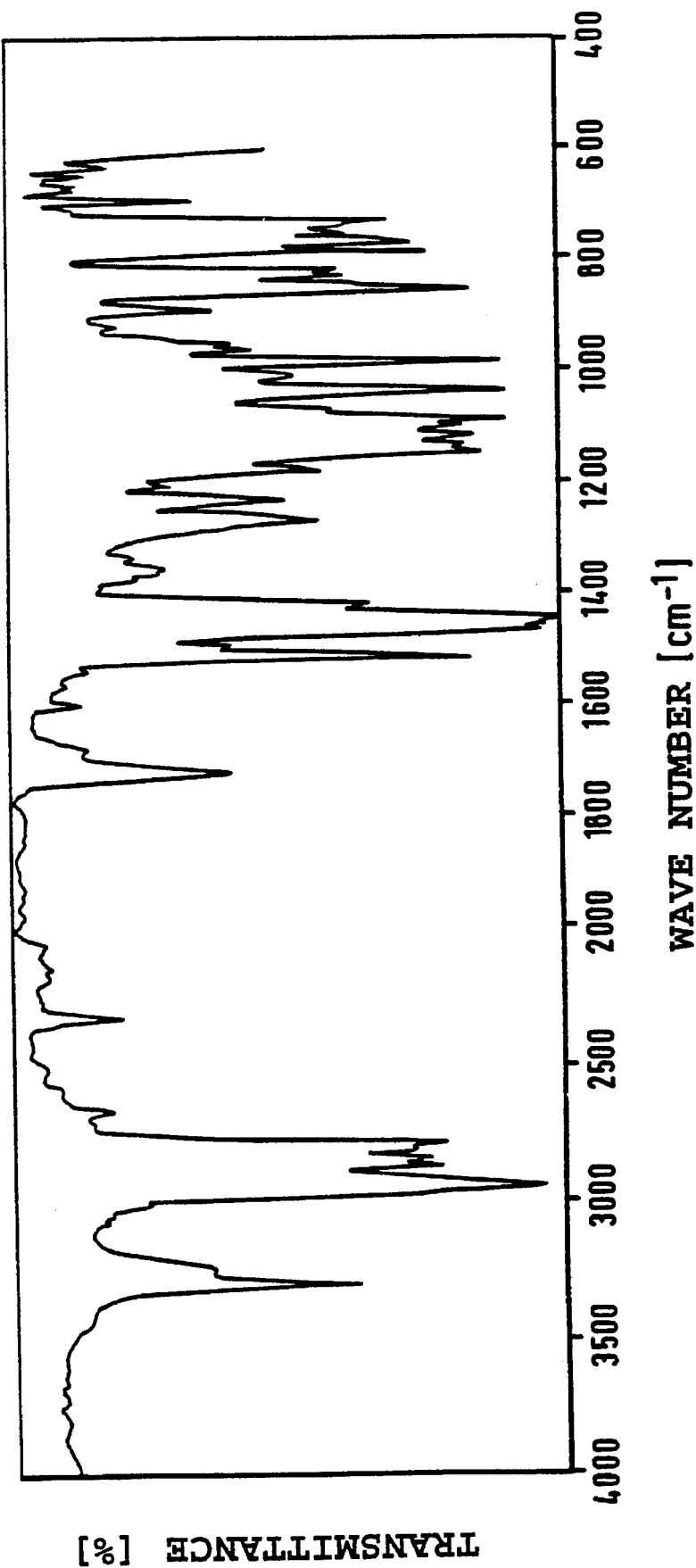
*Fig. 28* IR spectrum Diaddition compound no. 23 K

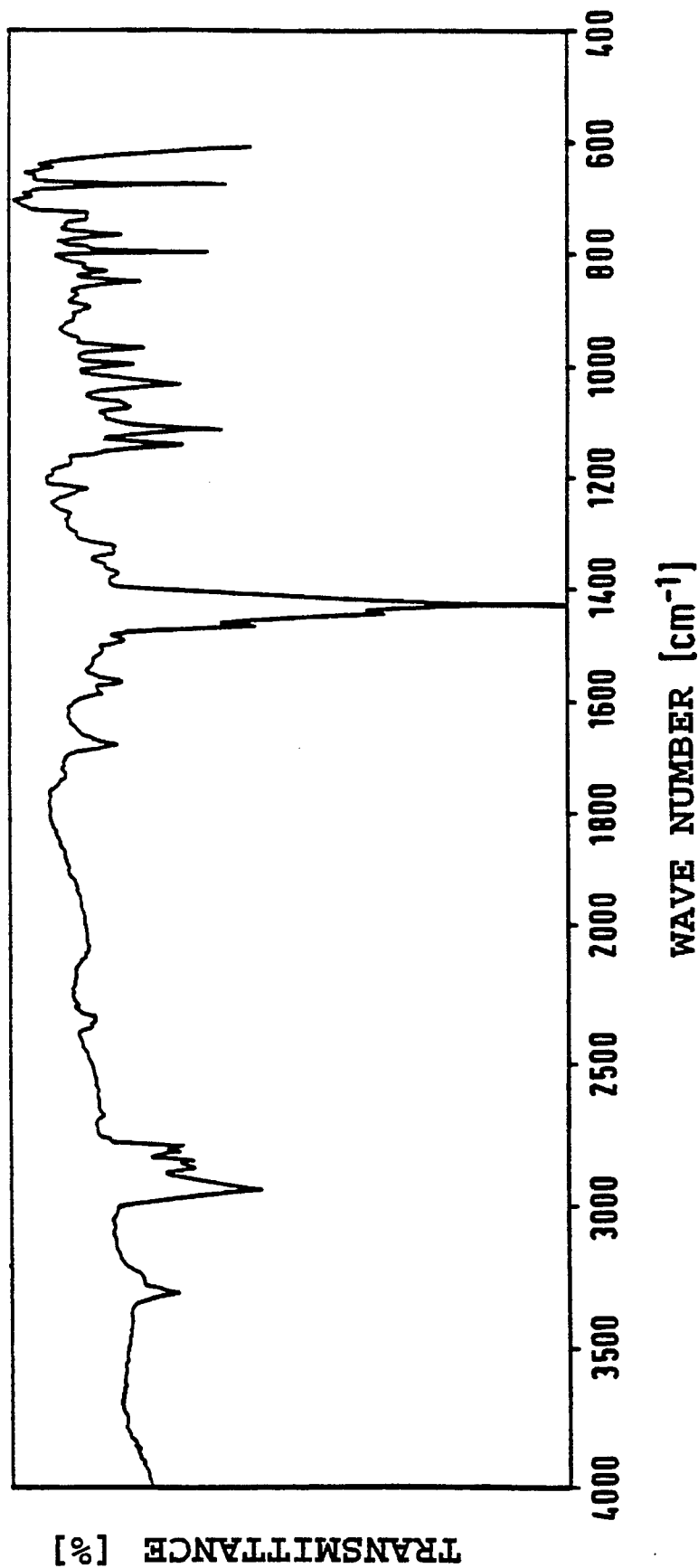
Fig. 29  IR spectrum  Monoaddition compound no. 24

FULLERENE DERIVATIVES, METHOD OF SYNTHESIZING THEM AND THEIR USE

This is a national stage application under 35USC 371 of international application Pct/EP93/02306 filed Aug. 26, 1993.

FIELD OF THE INVENTION

The invention relates to new addition compounds of diamines with fullerenes $C_{60}$ and/or $C_{70}$ and also a process for their preparation and their use.

BACKGROUND OF THE INVENTION

Since the discovery of fullerenes, a third modification of carbon, and particularly since their preparation has been possible, work has been carried out worldwide with an increasing tendency toward their chemical modification. This is particularly true of the most stable fullerene molecule $C_{60}$ which is also the one most readily obtainable in workable amounts (L. F. Lindoy, Nature, Vol. 357, 443 (1992); R. M. Baum, Chemical a. Engineering News 1991, Vol. 69, No. 50, p. 17).

Besides a series of different chemical reactions on the fullerene $C_{60}$, the addition of amines to the $C_{60}$ molecule has also already been reported [F. Wudl et al. in "Fullerenes: Synthesis, Properties and Chemistry of Large Carbon Clusters, Edit. G. S. Hammond and V. J. Kuck, ACS Symposium-Series, 481; Washington, D.C., 1992, p. 161; R. Seshadri, A. Govindaraj, R. Nagarajan, T. Pradeep and C. N. R. Rao, Tetrahedron Letters 33, No. 15, 2069 (1992)]. $C_{60}$ is a polyfunctional molecule. A significant disadvantage in the reported reactions is the formation of complex mixtures, which cannot be separated by conventional methods, in the reaction of the polyfunctional $C_{60}$ with amines. In almost every case, the reactions carried out in the manner reported hitherto give a myriad of different reaction products from which pure individual substances can only be isolated with unjustifiably great effort, if at all [A. Hirsch, Angew. Chem. 104 (1992), 808].

At present there are no known chemical reactions of nucleophiles with fullerenes which, when carried out in a conventional industrial manner, lead directly to uniform compounds or even to monoadducts or for which the subsequent application of conventional separation techniques, such as recrystallization or column chromatography, enables uniform compounds, in particular monoadducts, to be obtained from the mixtures formed. In "Tetrahedron Letters 33, page 2069 (1992)" mention is indeed made, inter alia, of obtaining a virtually pure 1:1 adduct of n-butylamine with $C_{60}$, but apart from information about IR and UV absorption bands, no material data are reported and no information is given on the elemental composition based on analytical results and on the isolation of such a fullerene derivative.

SUMMARY OF THE INVENTION

It has now surprisingly been found that the action of diamines, preferably disecondary diamines, on fullerene, forms addition compounds of the diamine with fullerene, among which the monoaddition compound and diaddition compounds represent the main products, which can very easily, using conventional separation methods, be separated and separated from multiple-addition compounds and thus be isolated in pure form.

The invention accordingly provides addition compounds obtainable by reaction of diamines of the formula I,

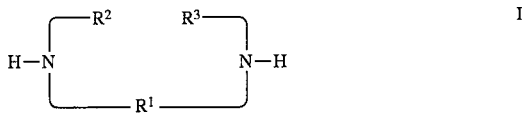

where
$R^1$ is $(C_2-C_4)$-alkylene or 1,2- or 1,3-cyclo-$(C_3-C_7)$-alkylene and
$R^2$ and $R^3$ are, independently of one another, hydrogen or $(C_1-C_3)$-alkyl or
$R^2$ and $R^3$ together are $(C_2-C_4)$-alkylene, with fullerene $C_{60}$ and/or $C_{70}$.

BRIEF DESCRIPTION OF THE DRAWINGS

FIG. 1 illustrates a graphical representation of an IR spectrum of a monoaddition compound according to one embodiment of the invention.

FIG. 2 illustrates a graphical representation of a Raman spectrum of a monoaddition compound according to one embodiment of the invention.

FIG. 3 is a graphical representation of a UV spectrum of a monoaddition compound according to one embodiment of the invention.

FIG. 4 is a graphical representation of an IR spectrum of an addition compound according to one embodiment of the invention.

FIG. 5 is a graphical representation of a UV spectrum of an addition compound according to one embodiment of the invention.

FIG. 6 is a graphical representation of an IR spectrum of a hydrochloride of a monoaddition compound according to one embodiment of the invention.

FIG. 7 is a graphical representation of a UV spectrum of an addition compound according to one embodiment of the invention.

FIG. 8 is a graphical representation of an IR spectrum of an addition compound according to one embodiment of the invention.

FIG. 9 is a graphical representation of an IR spectrum of a diaddition compound according to one embodiment of the invention.

FIG. 10 is a graphical representation of an IR spectrum of a diaddition compound according to one embodiment of the invention.

FIG. 11 is a graphical representation of an IR spectrum of a diaddition compound according to one embodiment of the invention.

FIG. 12 is a graphical representation of an IR spectrum of a monoaddition compound according to one embodiment of the invention.

FIG. 13 is a graphical representation of an IR spectrum of a diaddition compound according to one embodiment of the invention.

FIG. 14 is a graphical representation of an IR spectrum of a monoaddition compound according to one embodiment of the invention.

FIG. 15 is a graphical representation of an IR spectrum of a diaddition compound according to one embodiment of the invention.

FIG. 16 is a graphical representation of an IR spectrum of a diaddition compound according to one embodiment of the invention.

FIG. 17 is a graphical representation of an IR spectrum of a diaddition compound according to one embodiment of the invention.

FIG. 18 is a graphical representation of an IR spectrum of a diaddition compound according to one embodiment of the invention.

FIG. 19 is a graphical representation of an IR spectrum of a diaddition compound according to one embodiment of the invention.

FIG. 20 is a graphical representation of an IR spectrum of a diaddition compound according to one embodiment of the invention.

FIG. 21 is a graphical representation of an IR spectrum of a diaddition compound according to one embodiment of the invention.

FIG. 22 is a graphical representation of an IR spectrum of a monoaddition compound according to one embodiment of the invention.

FIG. 23 is a graphical representation of an IR spectrum of a monoaddition compound according to one embodiment of the invention.

FIG. 24 is a graphical representation of an IR spectrum of a monoaddition compound according to one embodiment of the invention.

FIG. 25 is a graphical representation of an IR spectrum of a monoaddition compound according to one embodiment of the invention.

FIG. 26 is a graphical representation of an IR spectrum of a monoaddition compound according to one embodiment of the invention.

FIG. 27 is a graphical representation of an IR spectrum of a monoaddition compound according to one embodiment of the invention.

FIG. 28 is a graphical representation of an IR spectrum of a diaddition compound according to one embodiment of the invention.

FIG. 29 is a graphical representation of an IR spectrum of a monoaddition compound according to one embodiment of the invention.

DESCRIPTION OF THE PREFERRED EMBODIMENTS

The structure of the monoaddition compound of the invention, in which $R^1$, $R^2$ and $R^3$ are as defined for formula I, is given by formula II. The diamine of the formula I is bonded via its two nitrogen atoms to adjacent carbon atoms of a bond lying between two six-membered rings of the soccer-ball-like fullerene skeleton, i.e. on the fullerene surface. This bond between two six-membered rings of the $C_{60}$ or $C_{70}$ will hereinafter be referred to as a "6—6 bond". The structure of the $C_{60}$ monoadducts of the invention of formula II, in which $R^1$, $R^2$ and $R^3$ are as defined for the formula I, is the structure having the greatest possible symmetry. The $^1$H-NMR, $^{13}$C-NMR and mass spectra indicate that the two hydrogen atoms formally introduced from the diamine of the formula I during the course of addition have been eliminated by dehydrogenation. Signals of hydrogen-bearing $C_{60}$ atoms occur neither in the $^1$H-NMR nor in the $^{13}$C-NMR spectra. The structure of the diaddition compounds, which are formed as regioisomers, is analogous to that of the monoadducts. As a result of the polyfunctionality of $C_{60}$ and $C_{70}$, a number of regioisomeric diaddition compounds are possible. The mass spectra and the $^1$H-NMR and $^{13}$C-NMR spectra of the diadducts demonstrate that these too are completely dehydrogenated fullerene derivatives, i.e. both hydrogen atoms introduced per diamine of the formula I have been eliminated. This means that there are no hydrogen atoms present which are bonded to the fullerene skeleton. By way of example, a structure of a diaddition compound arbitrarily selected from among the regioisomeric structures is shown in formula III, in which $R^1$, $R^2$ and $R^3$ are as defined for formula I.

The structure of the diaddition compound of the formula III is, as regards the relative spacing of the diamine units, selected arbitrarily. For diaddition compounds, a number of other relative structures is possible.

The relative spacing of the two diamine units is not subject matter of the structural observations presented in this description and is not fixed in the direaction or diaddition products to be obtained according to the invention and has not been determined in the direaction products described in the preparative examples.

The same applies to the structures of higher addition compounds, i.e. for those in which more than two diamine units are bonded per $C_{60}$ or $C_{70}$.

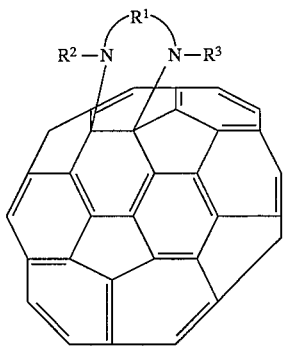

Formula II

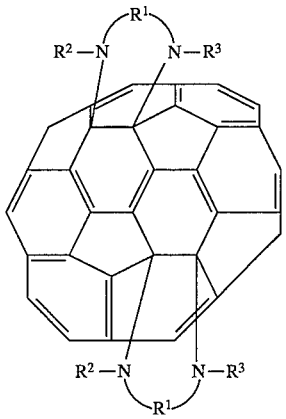

Formula III

The reaction of the invention is advantageously carried out using pure fullerene $C_{60}$ or $C_{70}$ or using fullerenes which contain at least 95% of $C_{60}$ or $C_{70}$. The reaction of the invention is preferably carried out using $C_{60}$ having a purity of >95% or pure $C_{60}$.

The reaction of the invention is preferably carried out using diamines of the formula I, in which $R^1$ is $—(CH_2)_2—$,

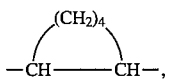

$R^2$ and $R^3$ are, independently of one another, hydrogen, $CH_3$ or $C_2H_5$ or $R^2$ and $R^3$ together are —$(CH_2)_2$— or —$(CH_2)_3$—.

Diamines which are particularly preferred for the reaction of the invention are N,N'-dimethylethylenediamine, N-methyl-N'-ethylethylenediamine, N,N'-diethylethylenediamine, N,N'-dimethyltrimethylenediamine, piperazine, homopiperazine, N-methylethylenediamine and N-ethylethylenediamine.

The reaction of the invention between the diamine of the formula I and $C_{60}$ and/or $C_{70}$ is preferably carried out in solution, i.e. the fullerene to be reacted is preferably subjected to the addition reaction in dissolved form.

Solvents which can be used here are all those in which fullerene $C_{60}$ and/or $C_{70}$ is appreciably soluble. Solvents which are advantageously used are aromatic hydrocarbons, aromatic halogen compounds or aromatic ethers, such as, for example, benzene, toluene, xylenes, mesitylene, ($C_2$–$C_4$)-alkylbenzenes, tetralin, naphthalene, 1- and/or 2-methylnaphthalene, dimethylnaphthalenes, ($C_2$–$C_6$)-alkylnaphthalenes, fluoro-, chloro-, dichloro-, trichloro and/or bromobenzene, anisole, phenetole, nerolin, ethoxynaphthalene, 1-chloronaphthalene and/or diphenyl ether and/or carbon disulfide. Preference is given to those aromatic hydrocarbons and/or halogen compounds which can be conveniently distilled off from the reaction mixture at atmospheric pressure or under reduced pressure at temperatures of up to 150° C., and also anisole.

The aromatic solvents can have further solvents mixed into them, advantageously in such an amount that fullerene $C_{60}$ and/or $C_{70}$ still remains appreciably soluble. Examples of such solvents which can be mixed in are aliphatic and/or cycloaliphatic hydrocarbons which are liquid at room temperature and boil at below 150° C., mono-, di-, tri- and/or tetrachloroalkanes and/or analogously chlorinated alkenes.

In the reaction of the invention, tertiary amines such as, for example, 1,4-diazabicyclo[2.2.2] octane, can be added as basic additives, namely in molar proportions of from 0.05 to 8.0 based on $C_{60}$ and/or $C_{70}$. These basic additives are advantageous when only a small molar excess, if any, of the diamine of the formula I relative to $C_{60}$ and/or $C_{70}$ is used. These possible basic additives control the reaction rate to give a favorable selectivity for formation of monoaddition products.

In the addition according to the invention of the diamine of the formula I to fullerene $C_{60}$ and/or $C_{70}$, the molar ratio used between the diamine and the respective fullerene influences the composition of the fullerene diamine addition products, namely an increase in the diamine concentration in relation to the amount of fullerene used increases the proportion of multiple-addition products. Within a wide range of molar ratios of diamine to fullerene, for example from about 0.5 to about 20.0 or above, monoaddition product and diaddition products are formed as main products.

The ratio in which the monoaddition, the diaddition and multiple-addition or reaction products are formed also depends strongly on the structure of the diamine of the formula I which is used. Thus, in the reaction of piperazine and homopiperazine within the abovementioned range (0.5 to about 20.0) of the molar ratio of diamine to fullerene, the monoreaction product is formed very predominantly. In the case of N,N'-dimethylethylenediamine, in contrast, the predominant main products formed under these conditions are the monoreaction product and direaction product in comparable amounts. For ethylenediamine and N,N'-diethylethylenediamine, the multiple-reaction products predominate relative to molar monoreaction and direaction product(s) in the reaction of the invention under comparable reaction conditions.

The reaction of the invention of a diamine of the formula I with fullerene $C_{60}$ and/or $C_{70}$ can be carried out within a very wide temperature range. Thus, the reaction can be carried out, for example, between −30° C., preferably 0° C., and +300° C., preferably +160° C. The reaction can however also take place at higher or lower temperatures.

Likewise, the reaction of the invention can be carried out within a very wide concentration range, based on the concentration of $C_{60}$ and/or $C_{70}$ and the concentration of the diamine of the formula I in the respective solvent or solvent mixture. This concentration range extends from about $10^{-3}$ millimolar to the saturation concentration of the $C_{60}$ or $C_{70}$ in the solvent or solvent mixture used in each case. The reaction can, however, also be carried out at a fullerene concentration of $<10^{-3}$ millimolar or even in the presence of undissolved fullerene $C_{60}$ and/or $C_{70}$.

The reaction of the invention is preferably carried out between a diamine I and $C_{60}$ and/or $C_{70}$ at a concentration of from 0.2, in particular 0.6, to 5.5, in particular 3.5, millimole of $C_{60}$ or $C_{70}$ or ($C_{60}$+$C_{70}$) per liter.

The concentration of the diamine of the formula I in the reaction medium is determined by the molar ratio.

In the reaction of the invention, the reaction times can vary within a very wide range. First, there is the relationship, generally known in chemistry, between reaction time and reaction temperature, whereby increasing reaction temperature reduces the reaction time necessary. However, the reaction time necessary also depends on the concentration of the reactants, the diamine and $C_{60}$ and/or $C_{70}$, in the reaction medium and also on their mutual molar ratio. In general, times required for the reaction decrease with increasing concentrations of the reactants in the reaction medium and with increasing molar ratio between the diamine and $C_{60}$ and/or $C_{70}$. Since this molar ratio in turn influences the product spectrum obtained for the addition products of the invention, the intended course of the reaction, i.e. the product spectrum obtained, can be controlled via this molar ratio and the reaction time.

The greater the molar ratio of diamine of the formula I to $C_{60}$ and/or $C_{70}$ and the greater the concentration of the diamine in the reaction solution, the shorter the reaction times required become and the more multiple adducts of the respective diamine of the formula I used with $C_{60}$ and/or $C_{70}$ are formed in comparison with the monoadduct and diadducts which are usually obtained in the highest proportion.

The other way around, a small molar ratio of diamine to $C_{60}$ or $C_{70}$, for example from 0.5 to 2.5, and a low concentration of the reactants in the reaction solution, for example <2 millimolar, greatly increases the reaction time required and the proportion of the usually predominant monoadduct. In this way, the monoadduct can, under particular conditions, become essentially the only reaction product formed.

A preferred embodiment of the reaction of the invention therefore comprises adding to a 0.2–5.0 millimolar solution of $C_{60}$ and/or $C_{70}$ in an aromatic hydrocarbon, fluorinated hydrocarbon or chlorinated hydrocarbon which is liquid at room temperature or anisole or a mixture of such aromatic solvents which is liquid at room temperature, 0.5–10 times, preferably 0.5–5 times, the molar amount of a diamine of the formula I and leaving this mixture for from 0.3 to 30 days, preferably 2–14 days, at a temperature between 0° C., preferably 20° C., and 160° C., preferably 110° C. The known relationship of increasing reaction temperature being able to shorten the reaction times is applicable here.

Particularly preferred solvents are benzene, toluene, xylene, chlorobenzene, 1,2- and/or 1,3-dichlorobenzene and/or anisole.

Of course, it is possible for the molarity of the reaction solution and also the ratio of diamine of the formula I to $C_{60}$ and/or $C_{70}$ and the reaction time for the reaction according to the invention to be below or above the abovementioned limits, depending on how completely the valuable fullerene is to be utilized in the reaction and on which distribution of the addition products is desired.

The addition products of the diamine of the formula I with fullerene $C_{60}$ and/or $C_{70}$, which are formed according to the invention, are satisfactorily characterized by their chemical properties, chemical composition and their spectroscopic data.

Among the chemical properties, the behavior on chromatography, such as conventional thin-layer and column chromatography and also HPLC, serves to characterize the new compounds formed. The number of base equivalents per defined new adduct also characterize, in combination with the chemical composition, the new compounds of the invention.

The chemical composition of the new fullerene derivatives of the invention is obtained from elemental analyses. For uniform adducts of the invention of a diamine of the formula I with $C_{60}$ and/or $C_{70}$, these analyses show whether a monoadduct or a multiple adduct, for example a di-, tri-, tetra-, penta- or hexaadduct or a higher adduct is present.

Furthermore, the spectroscopic data of the new compounds of the invention are particularly useful in their unambiguous characterization. These include the absorption spectra in the UV, visible and IR regions. The uniform addition compounds of the invention show characteristic IR spectra having a sharp bend structure. Likewise, the compounds of the invention each have characteristic UV absorptions, i.e. they differ in the position of their maxima.

The mass spectra, recorded using the FABMS (fast atom bombardment) technique likewise characterize the respective compounds and confirm the molecular weights, insofar as the molecular peak is present or can be inferred.

The NMR spectra too, measured both on solids and solutions, are also used for the characterization and structure assignment of the compounds of the invention.

Thus, for example, the IR spectrum of a monoaddition or a diaddition compound of a diamine I of the invention, in which $R^1$ and also $R^2$ and $R^3$ are as defined above except for hydrogen, with $C_{60}$ shows no N-H bands. This characteristic demonstrates that both nitrogen atoms of the diamine of the formula I are bonded to carbon atoms of the fullerene.

The new fullerene addition compounds formed according to the invention can be present in the reaction mixture in dissolved and/or undissolved form, depending on the solvent or solvent mixture used and on the temperature.

In the preferred embodiments of the reaction of the invention, which are carried out at a total concentration of the two reaction participants (starting materials), i.e. fullerene $C_{60}$ and/or $C_{70}$ and the diamine of the formula I, of <25 mmolar in benzene, toluene, xylene, tetralin, ethylbenzene, 1,2-dichlorobenzene and/or anisole, with or without addition of naphthalene, the new monoaddition and diaddition compounds formed are generally present, at a temperature between 0° C. and 110° C., in dissolved or substantially dissolved form.

For the purposes of isolation and purification, the new addition compounds formed, primarily the monoaddition compounds, can be partially precipitated as crystalline materials by evaporation of the reaction solution and as such can be isolated in a customary manner, e.g. by filtration.

A preferred embodiment for isolating and purifying the addition compounds of the invention comprises separating the reaction mixture, either directly or after prior filtration, by column chromatography, preferably on silica gel, into any unreacted fullerene $C_{60}$ and/or $C_{70}$ and the addition compounds formed. The column chromatography is advantageously carried out on silica gel using toluene and dichloromethane and dichloromethane/methanol mixtures as eluant. In this procedure, fullerene $C_{60}$ and/or $C_{70}$, is still present, if eluted first. This is followed, sharply delineated, by the respective monoaddition product and then, clearly spaced since they are more polar, any diaddition and multiple-addition compounds formed. It is also, on the other hand, possible to carry out such chromatographic separations using reversed phase (RP) silica gel or $Al_2O_3$ or other adsorbents as stationary phase.

After evaporation of the eluant, the addition compounds of the invention are obtained as solid, frequently crystalline materials. The latter is particularly the case for the monoaddition and diaddition compounds. Among these, the monoaddition product formed by action of piperazine ($R^1$ and also $R^2$ and $R^3$ together each —$(CH_2)_2$—) on $C_{60}$ has a particularly high tendency to crystallize.

This separation and purification of new fullerene derivatives into mono-, di- and multiple-addition compounds, which can be achieved by simple column chromatography, is exceptionally surprising. It is precisely the formation of complex mixtures from which it is virtually impossible to isolate individual compounds which is a very burdensome or disadvantageous characteristic of the fullerene chemistry known hitherto [A. Hirsch, A. Soi and H. R. Karfunkel, Angew. Chem. 104 (1992), 808]. The above-cited publication by A. Hirsch shows what great effort is necessary to be able to prepare and isolate a monoreaction product of fullerene $C_{60}$ in a suitable manner by means of a combination of analytical and preparative high-pressure liquid chromatography (HPLC).

It is (also) a feature of this invention that it provides a simple formation route to monoaddition compounds of $C_{60}$ and/or $C_{70}$, in particular of $C_{60}$, and that the reaction products, in particular the mono- and direaction products, can be isolated in pure form in such a simple and inexpensive way by conventional column chromatography, i.e. without use of high-pressure liquid chromatography which requires complicated apparatus and is suitable only for the preparation of small amounts. The addition compounds of the invention which are obtained by column chromatography or by other workup methods can, if necessary, be further purified by recrystallization.

Although, for the purposes of the present invention, the use of HPLC technology is surprisingly not necessary for the separation, isolation and purification of the compounds of the invention, the HPlC technique is suitable for characterizing the addition compounds obtained according to the invention. Retention time together with the stationary phase used and the liquid phase, the flow rate and also the usual column parameters serve as reliable material parameters for the characterization of pure substances of the invention or even mixtures.

A further advantage of the workup of the reaction mixture by column chromatography, which is possible according to the invention, is that any unreacted $C_{60}$ and/or $C_{70}$ is simply and cleanly separated off and can thus be recovered for reuse. In view of the high price of fullerene $C_{60}$ and/or $C_{70}$, this is of considerable importance.

The addition compounds of diamines of the formula I, in which $R^1$, $R^2$ and $R^3$ are as defined above, with $C_{60}$ and/or $C_{70}$ which are obtainable according to the present invention are basic compounds and form acid-addition salts with protic acids, reacting with at least 1 equivalent of acid per unit of diamine added to fullerene $C_{60}$ and/or $C_{70}$. This means that, for example, a monoaddition compound can bind at least 1 equivalent of acid, and a diaddition compound can bind at least 2 equivalents of acid, to form acid-addition salts. With hydrochloric acid, for example, a hydrochloride is formed from the monoaddition compound of piperazine with $C_{60}$. These acid-addition salts of the fullerene derivatives obtainable according to the invention are likewise subject matter of this invention.

The acid-addition salts are considerably less soluble in nonpolar solvents than the corresponding bases. Thus, for example, addition of etherical hydrochloric acid to a solution of the monoaddition product formed from piperazine and $C_{60}$ in anisole results in virtually quantitative precipitation of the corresponding hydrochloride.

For the preparation of acid-addition salts of the fullerene derivatives of the invention, all intermediate-strength and strong acids are suitable in principle.

The disecondary diamines of the formula I required as starting materials are known or can be prepared by known methods. Fullerenes $C_{60}$ and $C_{70}$ are likewise prepared by known methods [W. Krätschmer, L. D. Lamb, K. Fostiropoulos, D. R. Huffman, Nature 1990, 347, 354; W. Krätschmer, K. Fostiropoulos, D. R. Huffman, Chem. Phys. Lett. 1990, 170, 167; H. Ajie, M. M. Alvarez, S. J. Anz, R. D. Beck, F. Diederich; K. Fostiropoulos, D. R. Huffman, W. Krätschmer, Y. Rubin, K. E. Schriver, D. Sensharma, R. L. Wetten, J. Phys. Chem. 1990, 94, 8630].

The fullerene derivatives of the invention are suitable for use as complex ligands. This property can be used for modifying catalysts.

In addition, the compounds of the invention can be used for the inhibition of enzymes, for example for the inhibition of HIV (human immunodeficiency virus)-enzymes such as HIV-1 protease, and thus represent biological active compounds which can, for example, be used as antiviral agents.

Furthermore, the addition compounds are electrically conductive in the solid state. Thus, for example, conductive casings of this material can be applied from solution.

The monoaddition compound obtained by action of piperazine on $C_{60}$ shows intrinsic conductivity.

The following examples illustrate the invention, without restricting it to the conditions specified by way of example.

Unless otherwise mentioned in the following examples, column chromatography was carried out on Kieselgel S, particle size from 0.063 to 0.2 mm, from Riedel-de Haen AG, Seelze and thin-layer chromatography on Kieselgel 60 $F_{254}$ (layer thickness 0.25 mm) from Riedel-de Haen AG, Seelze.

High-pressure liquid chromatography (HPLC) was carried out using a Hewlett-Packard apparatus "HP 1090 Series II Liquid Chromatograph" having a "Hewlett Packard HP 1040 A Diode-Array Detector" at 256 nm (band width 4 nm).

Furthermore, the solvent mixtures used in the column chromatography which are not specified in more detail are $CH_2Cl_2/CH_3OH$ mixtures.

EXAMPLE 1

Under a blanket of nitrogen, a solution of 1100 mg $C_{60/70}$ (97.25:2.75) in 592 ml of toluene was admixed at room temperature (RT) with a solution of 1035 mg of piperazine in 183 ml of toluene and the mixture was stirred for 45 hours at 50° C. and 96 hours at room temperature. The reaction mixture was then filtered through a filter aid and the filtrate was applied to or filtered through a Kieselgel S (0.063 to 0.2 mm) $CH_2Cl_2$ column (H:38; φ3.6 cm). After the filtered reaction solution had been drawn in, elution was continued using $CH_2Cl_2$. The first 1200 ml of eluate contained (after evaporation in vacuo, digestion of the residue in 40 ml of ether, filtration with suction and drying) 192 mg (=17.5% of material used) of fullerene $C_{60>70}$. Elution was subsequently continued using $CH_2Cl_2/CH_3OH$ (100:0.8). After 2500 ml of substance-free eluate, 1530 ml of eluate containing a brown-black moving zone were selected. After evaporating the solvent of this fraction, digestion of the crystalline residue (560 mg) in 40 ml of ether and filtration by suction, there were obtained after drying (4 hours, 50° C., 2 millibar) 507 mg of crystalline product which is essentially pure (>97.5%) monoaddition compound of piperazine with $C_{60}$. The yield of this compound is, based on fullerene reacted, 50% of theory.

Molecular formula: $C_{64}H_8N_2$ (MW 804.78) calc. C 95.52H 1.00N 3.48% found C 95.0H 1.4N 3.2% found C 95.0H 0.8N 3.4%

The IR spectrum (recorded using an IR microscope. Powder on KBr) of this monoaddition compound formed from piperazine and $C_{60}$ is shown in FIG. 1 below.

The Raman spectrum of this monoaddition product is shown in FIG. 2. The mass spectrum (FAB) gives a molecular mass M=804 Dalton, indicated by two intense peaks, $MH^{\oplus}$ at m/e 805 and $M^{\ominus}$ at m/e 804.

Thin-layer chromatography (TLC) on Kieselgel 60/F 254, layer thickness 0.25 mm, from Riedel-de Haen, eluant: $CH_2Cl_2/C_2H_5OH$=10:1 (v/v): $R_F$: 0.58 to 0.63 (the monoaddition product runs significantly behind $C_{60}$ and significantly in front of all other fullerene derivatives also formed).

High-pressure liquid chromatography (HPLC): on LiChrospher® 100 RP-18 (5 µm), length 250×φ4 mm, eluant $CH_2Cl_2$/i-$C_3H_7OH$: 60:40+0.1% $(C_2H_5)_2NH$, flow 0.8 ml/min.; retention time: 3.85 min. (% by area 98.6). The UV spectrum of this monoaddition compound is shown in FIG. 3.

This monoaddition product of piperazine with $C_{60}$ (≡ described as addition compound No. 1) can be recrystallized from solvents and further purified in this way. It crystallizes in thin, long, dark-colored, strongly reflecting needles. Suitable solvents for this purpose are chlorobenzene, dichlorobenzene and/or anisole.

The new compound (No. 1) is sparingly soluble or essentially insoluble in benzene, toluene, $CHCl_3$, $CH_2Cl_2$ and $CH_3OH$, and soluble in $CS_2$.

After the main product described above (≡ addition compound No. 1) had been eluted from the column, elution was continued using $CH_2Cl_2/CH_3OH$ (100:2) and (100:4). After 600 ml of substance-free eluate, elution with 1000 ml (100:4) gave 33 mg of a second new addition compound of piperazine with $C_{60}$ (≡ addition compound No. 2) which was obtained in crystalline form from $CH_2Cl_2$ solution. Filtration with suction and drying (50° C., 3 mbar) of the crystalline product gave 10 mg of addition compound No. 2 in pure, crystalline form. This addition compound No. 2 proved to be a diaddition compound.

Molecular formula: $C_{68}H_{16}N_4$ (MW 888.91) calc. C 91.88H 1.81N 6.30% found C 90.1H 1.7N 6.0%

The IR spectrum (recorded using an IR microscope, powder on KBr) is shown in FIG. 4.

TLC ($CH_2Cl_2/C_2H_5OH$ 10:1) $R_F$: 0.42 to 0.48

HPLC: column, eluant as for addition compound No. 1, flow 0.8 ml/min. Retention time: 3.09 or 3.12 min. (% by area 98.4).

The UV spectrum of this addition compound No. 2 is shown in FIG. 5.

The mass spectrum gives a molecular mass M=888 Dalton, indicated by an intense $M^{\ominus}$ peak at m/e 888.

After the addition compound No. 2 had been eluted from the column, elution with $CH_2Cl_2/CH_3OH$ 100:4 (500 ml) gave 27 mg of product which proved to be a mixture of the diaddition compounds No. 2, No. 3, No. 3a and No. 4. Subsequent elution using 1200 ml (100:5) and 500 ml (100:6) gave 60 mg of a mixture of the diaddition compounds No. 3, No. 3a and No. 4. Crystallization of this mixture from $CH_2Cl_2$ gave 15 mg of an otherwise pure mixture of the diaddition compounds No. 3, No. 3a and No. 4 (approximately equal amounts) in crystalline form.

After the addition compounds No. 3, No. 3a and No. 4 had been eluted from the column, elution using $CH_2Cl_2/CH_3OH$ 100:7 (1000 ml) and 100:10 (1000 ml) gave 90 mg (evaporation residue) of the addition compound No. 5. This gave, from $CH_2Cl_2$, 43 mg of pure addition compound No. 5 in crystalline form (dried: 5 hours at 50° C., 3 to 4 mbar). This compound No. 5 is likewise a diaddition compound.

Molecular formula: $C_{68}H_{16}N_4$ (MW 888.91) calc. C 91.88H 1.81N 6.30% found C 85.7; 85.4H 2.1; 2.0N 5.9; 6.2%

The mass spectrum gives a molecular mass M=888 Dalton, indicated by an intense $MH^{\oplus}$ peak at m/e 889.

The IR spectrum of the pure diaddition compound No. 5 is shown in FIG. 8, the UV spectrum in FIG. 7.

TLC ($CH_2Cl_2/C_2H_5OH$ 10:1) $R_F$: 0.06 to 0.14

HPLC (conditions as for No. 1 and No. 2),

Retention time: 3.05 or 3.20 min. (% by area 93.5).

After elution of the diaddition compound No. 5, further polar substances can be eluted in small amounts using polar eluants, for example $CH_2Cl_2/CH_3OH$ 5:1 to 1:1.

EXAMPLE 2

Under a blanket of nitrogen, a solution of 184 mg of $C_{60/70}$ (96.7:3.3) in 200 ml of benzene was admixed at room temperature with a solution of 68.5 mg (0.795 mmol) of piperazine in 25 ml of benzene and the mixture was allowed to stand for 95 hours at from 25≅ to 27° C. It was subsequently stirred for a total of 41 hours at from 51° to 52° C. and was, in between, allowed to stand for a total of 125 hours at room temperature. The reaction solution was then filtered through a filter aid and applied to a Kieselgel S—$CH_2Cl_2$ column (H:30, ϕ2.9 cm). The column chromatography was carried out, in principle, in the same way as described in Example 1. The total amount of eluate was 4200 ml. This chromatography gave, in the same manner as described in Example 1: unreacted fullerene $C_{60/70}$ (about 97:3):89 mg (=48.4% of the amount used); addition compound No. 1 (monoaddition compound of piperazine with $C_{60}$): 72 mg (=67.4% yield based on reacted fullerene). A total of only 3 mg (unseparated) of further addition compounds running after this main reaction product during the column chromatography were obtained.

EXAMPLE 3

Under a blanket of $N_2$, a solution of 467 mg of $C_{60/70}$ (97.2:2.8) in 200 ml of toluene was admixed at room temperature with a solution of 34.5 mg (0.40 mmol) of piperazine in 40 ml of toluene and the mixture was allowed to stand for 11 days at from 26° C. to 32° C. The turbid reaction solution was filtered through Clarcel and applied to a Kieselgel S—$CH_2Cl_2$ column (H 24, ϕ2.4 cm). The column chromatography was carried out, in principle, in the same way as described in Example 1; the following overview shows the breakdown of the fractions and their content of eluted product.

| Fraction | Eluant | Vol. ml | Content (residue) in mg | |
|---|---|---|---|---|
| 1 | $CH_2Cl_2$ | 150 | — | Initial fraction, discarded |
| 2 | Toluene $CH_2Cl_2$ | 300 | 363 | Fullerene $C_{60>70}$ |
| 3 | $CH_2Cl_2/CH_3OH$, 100:0.8 | 1000 | — | Intermediate fraction |
| 4 | $CH_2Cl_2/CH_3OH$, 100:0.8 | –1000 | 143 | Addition compound No. 1 |
| 5 | $CH_2Cl_2/CH_3OH$, 5:1 | –1000 | 26 | A mixture of the diaddition compounds No. 2, 3, 3a, 4 and 5 |

The residue of the fraction 2 (363 mg) was suspended in 30 ml of ether, allowed to stand for 30 min. at room temperature and then filtered with suction, washed with ether and dried for 4 hours at 55° C., 3 to 4 mbar. This gave 336 mg (=72% of material used) of fullerene $C_{60/70}$.

The residue of the fraction 4 (143 mg) was treated likewise with ether, filtered with suction and dried: this gave 130 mg (=88.6% yield based on reacted fullerene) of the monoaddition compound of piperazine with $C_{60}$ (≡ addition compound No. 1) in microcrystalline form.

EXAMPLE 4 to 10

The Examples 4 to 10 which are shown below in tabular form were carried out, in principle, in the same way as the Examples 1, 2 and 3 which have been described in detail. This applies particularly to the column chromatography procedure.

In Example 6, the solvent used was a mixture of toluene and tetrahydrofuran (THF) and in Example 10 the solvent was a mixture of toluene and tetrachloroethylene. The diaddition compounds (No. 2, 3, 3a, 4 and 5), eluted after the monoaddition compound (of piperazine with $C_{60}$) (No. 1) in the respective column chromatography were in each case collected together, i.e. not separated into the individual diaddition compounds 2, 3, 3a, 4 and/or 5.

| | Fullerene | | | | Reaction | Recovered fullerene | | | | |
|---|---|---|---|---|---|---|---|---|---|---|
| Ex. No. | $C_{60/70}$ (.../...) mg | Piperazine mg | (mmol) | Solvent (ml) | time in days; at temp. [°C.] | mg | % of material used | Addition compound No. | mg | Yield*) [%] |
| 4 | 467 (97.2/2.8) | 157 | (1.82) | Toluene (334) | 2.0; 28–31 1.2; 69–78 | 225 | 48.2 | 1 2–5 | 242 5 | 89.3 |
| 5 | 241 (97.2/2.8) | 18 | (0.21) | Toluene (151) | 19.3; 27–36° | 206 | 85.4 | 1 2–5 | 28 30 | 71.0 |

-continued

| Ex. No. | Fullerene $C_{60/70}$ (../..) mg | Piperazine mg | (mmol) | Solvent (ml) | Reaction time in days; at temp. [°C.] | Recovered fullerene mg | % of material used | Addition compound No. | mg | Yield*[%] |
|---|---|---|---|---|---|---|---|---|---|---|
| 6 | 186 (97.2/2.8) | 33 | (0.38) | Toluene (105) THF (34) | 2.6; 50–52 8.2; 26–32 | 97 | 52.2 | 1 2–5 | 52 22 | 52.4 |
| 7 | 429 (96.8/3.2) | 487 | (5.65) | Toluene (425) | 11.0; 27–32 | 84 | 19.6 | 1 2–5 (#) | 190 80 110 | 49.2 |
| 8 | 287 (97.2/2.8) | 173 | (2.00) | Toluene (186) | 1.8; 90 5.0; 25–29 | 113 | 39.4 | 1 2–5 | 128 28 | 65.9 |
| 9 | 225 (97.2/2.8) | 134 | (1.56) | Anisole (133) | 2.5; 50–52 8.3; 22–28 | 23 | 10.2 | 1 2 3 + 4 5 | 89 22 28 20 | 39.3 |
| 10 | 168 (97.2/2.8) | 82 | (0.95) | Toluene (220) $Cl_2C=CCl_2$ (16) | 2.8; 76–78 8.7; 26–32 | 90 | 53.6 | 1 2–5 | 41 18 | 47.0 |

*)Yield is based on reacted fullerene $C_{60/70}$ (~97:3)
(#)Reaction products which are more polar than the diaddition compounds No. 2–5 are eluted from the column far behind No. 5.

EXAMPLE 11

Under a blanket of $N_2$, 85 mg of fullerene $C_{60/70}$ (97.2/2.8) were dissolved at 83° C. in 100 g of naphthalene. To this solution was added, at from 82° to 83° C., a solution of 21.5 mg (0.25 mmol) of piperazine in 3.1 ml of toluene and the mixture was stirred for 61.5 hours (with interruptions each night) at from 86° to 87° C. and for 151 hours at room temperature (from 24° to 29° C.). The reaction mixture was then diluted with 180 ml of toluene, cooled to room temperature and applied to a Kieselgel S/$CH_2Cl_2$ column (H:29; φ3.4 cm). Elution was carried out initially using $CH_2Cl_2$ (cf. tabular summary below) and then using $CH_2Cl_2$/$CH_3OH$ mixtures.

| Fraction | Eluant | Vol. ml | Content (residue) in g | |
|---|---|---|---|---|
| 1 | $CH_2Cl_2$; (toluene) | 300 | — | Initial fraction, discarded |
| 2 | $CH_2Cl_2$; (toluene) | 700 | 82.70 | Naphthalene + Fullerene $C_{60>70}$ |
| 3 | $CH_2Cl_2$ | 500 | — | Intermediate fraction |
| 4 | $CH_2Cl_2$/$CH_3OH$ 100:0.6 | 500 | — | Intermediate fraction |
| 5 | $CH_2Cl_2$/$CH_3OH$ 100:0.8 | 500 | — | Intermediate fraction |
| 6 | $CH_2Cl_2$/$CH_3OH$ 100:0.8 | 800 | 0.033 | Addition compound No. 1 |
| 7 | $CH_2Cl_2$/$CH_3OH$ 10:1 | 500 | 0.010 | Mixture of the diaddition compounds No. 2, 3, 3a, 4 and 5 |
| 8 | $CH_2Cl_2$/$CH_3OH$ 10:1.5 | 500 | 0.006 | Mixture of the diaddition compounds no. 2, 3, 3a, 4 and 5 |

The naphthalene was distilled from the residue of fraction 2 in a bulb tube (0.05 mbar, 80° bath temperature). 114 mg of residue remained. This was suspended for 30 minutes in 25 ml of ether and filtered off with suction after standing for 30 minutes, washed with ether and dried for 4 hours at 52° C. and from 3 to 4 mbar.

This gave back 48 mg (=56.5% of material used) of fullerene $C_{60>70}$.

The residue from fraction 6 (33 mg) was suspended in 20 ml of ether, filtered off with suction after standing for 1 hour, washed with ether and dried (4 hours, 52°, 3 to 4 mbar). This gave 28 mg (=67.6% yield based on reacted fullerene) of pure monoaddition compound (addition compound No. 1).

The residue of the fractions 7+8 (16 mg) comprised the diaddition compounds No. 2, 3, 3a, 4 and 5.

EXAMPLE 12

Hydrochloride of the monoaddition compound of piperazine with $C_{60}$:

81 mg (0.1 mmol) of the monoaddition compound (addition compound No. 1) of piperazine with $C_{60}$ were dissolved at 110° C. in 30 ml of anisole. This solution was cooled without stirring to 50° C. At this temperature, 0.36 ml of a 0.61 molar solution of HCl in ether were added with stirring (below the liquid surface). Solid was immediately formed as a light brown precipitate. The mixture was stirred for a further 30 min., with the temperature falling from 50° C. in the direction of room temperature, the solid was then filtered off with suction, washed with 5 ml of anisole and with plenty of ether and was dried for 4 hours at 65° C. and from 3 to 5 mbar. This gave 80 mg of brown, crystalline solid which is a hydrochloride of the monoaddition compound of piperazine with $C_{60}$.

Elemental analysis: found C 89.2H 2.0 Cl4.6; 4.8N 3.1% for $C_{64}H_9ClN_2$ (MW 841.25) calc. C 91.38H 1.08 Cl 4.21N 3.33% for $C_{71}H_{17}ClN_2O$*) (MW 949.39) calc. C 89.82H 1.80 Cl 3.73N 2.95%

*)=hydrochloride containing 1×anisole as solvent of crystallization.

The IR spectrum of the hydrochloride obtained is shown in FIG. 6.

EXAMPLE 13

Isolation of diaddition compounds of piperazine with $C_{60}$ by chromatography:

869 mg of a mixture of the diaddition compounds No. 2, No. 3, No. 3a and No. 4 formed from piperazine and $C_{60}$ were dissolved in 350 ml of $CH_2Cl_2$ and applied to a Kieselgel S/$CH_2Cl_2$ column (H:65; φ4 cm). Elution was carried out using, in succession, $CH_2Cl_2$ and $CH_2Cl_2$/

CH$_3$OH (100:1) (each 1000 ml) and (100:2; 2000 ml). After 4 liters of substance-free eluate, elution was continued using CH$_2$Cl$_2$/CH$_3$OH mixtures (100:2.2; 100:2.4; 100:2.6 and 100:2.8) (6×1000 ml). This eluate contained a total of 125 mg of a mixture of the compounds No. 2 and No. 4. Further elution using 2 l (100: 2.8) gave 110 mg of a virtually pure compound No. 4 as evaporation residue. This was dissolved in hot toluene, the solution was filtered and again evaporated in vacuo. The residue was digested with ether and the crystalline material was filtered off with suction. After drying (4 hours at 50° C., 3–5 mbar), 65 mg of TLC-pure diaddition compound No. 4 were obtained.

Molecular formula: C$_{68}$H$_{16}$N$_4$ (MW 888.91) calc. C 91.88H 1.81N 6.30% found C 89.8H 2.3N 6.2%

The mass spectrum gives a molecular mass M=888 Dalton, indicated by an intense MH$^\oplus$ peak at m/e 889.

The IR spectrum (recorded using an IR microscope, powder on KBr) of this diaddition compound (No. 4) formed from piperazine and C$_{60}$ is shown in FIG. 11. Thin-layer chromatography (TLC) (CH$_2$Cl$_2$/C$_2$H$_5$OH 10:1) R$_F$ 0.22–0.25.

After elution of pure compound No. 4, elution was continued using CH$_2$Cl$_2$/CH$_3$OH (100:3). 1000 ml of eluate gave 110 mg of a mixture of the direaction products No. 3 and No. 4. 1500 ml of further eluate gave 173 mg of enriched compound No. 3 containing a small amount of compound No. 4 as residue. After digestion with ether and filtration with suction and drying of the crystalline material, 128 mg of enriched compound No. 3 were obtained. This substance was dissolved in a mixture of 30 ml of toluene, 20 ml of CH$_2$Cl$_2$ and 20 ml of CH$_3$OH. The CH$_2$Cl$_2$ and CH$_3$OH were then largely drawn off in vacuo. Crystallization occurred from the remaining solution. The crystalline product was filtered off with suction, washed with toluene and ether and dried for 4 hours at 50° C., 5 mbar. This gave 55 mg of almost pure, according to TLC, diaddition compound No. 3.

Molecular formula: C$_{68}$H$_{16}$N$_4$ (MW 888.91) calc. C 91.88H 1.81N 6.30% found C 90.2H 2.0N 6.1%

The mass spectrum gives a molecular mass M=888 Dalton, indicated by an intense MH$^\oplus$ peak at m/e 889 and a M$^\ominus$ peak at m/e 888.

The IR spectrum (recorded as for No. 4) of this diaddition compound (No. 3) formed from piperazine and C$_{60}$ is shown in FIG. 9. Thin-layer chromatography (TLC) (CH$_2$Cl$_2$/C$_2$H$_5$OH 10:1) R$_F$ 0.26–0.30.

After elution of enriched compound No. 3, elution was continued using CH$_2$Cl$_2$/CH$_3$OH (100:4; 100:5 and 100:6) (each 1000 ml). These fractions contained 275 mg of a mixture (about 1:1) of the diaddition compounds No. 3 and No. 3a. These 275 mg of mixture were partially separated into the pure diaddition compounds No. 3 and No. 3a in a further column chromatography step (cf. Example 14 below)

EXAMPLE 14

275 mg of an approximately 1:1 mixture of the diaddition compounds No. 3 and No. 3a formed from piperazine and C$_{60}$ (obtained as a last fraction in the chromatography described in Example 13) were dissolved in 280 ml of toluene and applied to a Kieselgel S/toluene column (H:42; ϕ3 cm). Elution was carried out using, in succession, toluene/methanol mixtures (100:0.5; 100:0.75; 100:1; 100:1.1) (each 500 ml). These 2 l of eluate contained 6 mg of virtually new, according to TLC, diaddition compound No. 3 (data cf. Example 13). Elution was then continued using toluene/methanol 100:1.2; 100:1.4 and 100:1.6 (each 1000 ml). These fractions contained 187 mg of a mixture of the compounds No. 3 and No. 3a. Elution was then continued in a similar way using 100:1.8 and 100:2 (each 1000 ml). This last fraction gave 25 mg of almost pure diaddition compound No. 3a.

Molecular formula: C$_{68}$H$_{16}$N$_4$ (MW 888.91) calc. C 91.88H 1.81N 6.30% found C 90.1H 2.0N 6.1%

The mass spectrum gives a molecular mass M=888 Dalton, indicated by an intense M$^\ominus$ peak at m/e 888 and MH$^\oplus$ peak at m/e 889.

The IR spectrum (powder on KBr) of this addition compound No. 3a is shown in FIG. 10. Thin-layer chromatography (TLC) (CH$_2$Cl$_2$/C$_2$H$_5$OH 10:1) R$_F$ 0.20–0.25.

EXAMPLE 15

Under a blanket of nitrogen, a solution of 360 mg of C$_{60/70}$ (96.8:3.2) in 210 ml of toluene was admixed at RT with a solution of 396 mg of homopiperazine in 50 ml of toluene and was stirred for 3.1 days at 60° C. and for 10 days at RT. After filtration, the solution was applied to a Kieselgel S(0.063 to 0.2 mm)—CH$_2$Cl$_2$ column (H: 43; ϕ2.9 cm) and filtered through it. After withdrawal of the filtered reaction solution, elution was continued using CH$_2$Cl$_2$. The first 1000 ml of eluate contained (after evaporation in vacuo, digestion of the residue in 20 ml of ether, filtration with suction and drying) 10 mg (≡2.8% of material used) of fullerene C$_{60>70}$. Subsequently, elution was continued using CH$_2$Cl$_2$/CH$_3$OH (100:0.2 to 0.4). After 500 ml of substance-free eluate, 1000 ml of eluate containing a brown-black moving zone were selected. After evaporation of the solvent of this fraction, digestion of the crystalline residue (194 mg) in 40 ml of ether and filtration with suction, there were obtained, after drying (4 hours, 50° C., 2 millibar), 160 mg of a crystalline product which is the pure monoaddition compound No. 7 of homopiperazine with C$_{60}$. The yield of this compound is, based on reacted fullerene, 40% of theory.

Molecular formula: C$_{65}$H$_{10}$N$_2$ (MW 818.81) calc. C 95.35H 1.23N 3.42% found C 94.7H 1.1N 3.4%

The IR spectrum (recorded using an IR microscope. Powder on KBr) of this monoaddition compound No. 7 formed from homopiperazine and C$_{60}$ is shown in FIG. 12.

The mass spectrum (FAB) shows a molecular mass M=818 (intense MH$^\oplus$ peak at m/e 819).

Thin-layer chromatography (TLC) on Kieselgel 60/F 254, layer thickness 0.25 mm, from Riedel-de Haen, eluant: CH$_2$Cl$_2$/C$_2$H$_5$OH=10:1 (v/v): R$_F$: 0.61 to 0.64 (the monoaddition product runs closely behind C$_{60}$ and significantly in front of all other fullerene derivatives formed).

High-pressure liquid chromatography (HPLC): on Shandon Hypersil (5 μm), length 250×ϕ4 mm, eluant CH$_2$Cl$_2$/C$_2$H$_5$OH; gradient flow 1.5 ml and 2.0 ml/min.; retention time: 5.66 min. (% by area >98.5).

This monoaddition product of homopiperazine with C$_{60}$ (≡ referred to as addition compound No. 7) can be recrystallized from solvents and further purified in this way. Suitable solvents for this purpose are chlorobenzene, dichlorobenzene and/or anisole.

The new compound (No. 7) is sparingly soluble in benzene, toluene, CHCl$_3$, CH$_2$Cl$_2$ and CH$_3$OH, but readily soluble in CS$_2$.

After the above-described main product (≡ addition compound No. 7) had been eluted from the column, elution was continued using $CH_2Cl_2/CH_3OH$ (100:1). After 500 ml of substance-free eluate, elution using 1000 ml (100:1.5) gave 15 mg of a further addition compound of homopiperazine with $C_{60}$ ($\equiv$ addition compound No. 8) which was obtained in crystalline form after digestion with ether. After filtration with suction and drying (50° C., 3 mbar) of the crystalline product, 13 mg of addition compound No. 8 were obtained.

TLC ($CH_2Cl_2/C_2H_5OH$ 10:1) $R_F$: 0.52 to 0.56

HPLC: column, eluant and flow as for addition compound No. 7, retention time in min. (% by area): 5.81 (64.1%); 6.09 (15.3%) and 6.25 (20.6%). HPLC thus shows that the 0addition compound No. 8 consists of 3 components. These are 3 regioisomeric diaddition compounds of homopiperazine with $C_{60}$. This is shown by the mass spectrum which indicates a molecular mass M=916 Dalton by means of an intense $MH^\oplus$ peak at m/e 917.

After the diaddition compound No. 8, consisting of 3 isomers, had been eluted from the column, elution using 500 ml each of $CH_2Cl_2/CH_3OH$ (100:2) and (100:2.2) gave 9 mg of a mixture of diaddition compounds. Subsequent elution using 500 ml (100:2.5) gave, as a sharp dark zone, 30 mg of addition compound from which 25 mg of addition compound No. 9 were obtained in crystalline form by crystallization from ether, after filtration with suction and drying.

HPLC: column, eluant and flow as for addition compound No. 7, retention time in min. (% by area): 6.58 (14.0%); 6.78 (11.2%) and 6.97 (68.5%); 6.3% by area correspond to the 3 isomers of the compound No. 8. Thus, this product No. 9 also consists of 3 isomers besides this proportion (6.3%) of the compound No. 8. The fact that compound No. 9 is a diaddition product consisting of 6 regioisomers is evidenced by the following C, H, N analysis.

Molecular formula: $C_{70}H_{20}N_4$ (MW 916.96) calc. C 91.69H 2.20N 6.11% found C 91.1H 2.1N 6.0%

The mass spectrum (FAB) shows a molecular mass M=916 (intense $M^\ominus$ peak at m/e 916 and $MH^\oplus$ peak at m/e 917); TLC ($CH_2Cl_2/C_2H_5OH$ 10:1) $R_F$: 0.45 to 0.47.

After elution of the diaddition compound No. 9 consisting of 3 isomers and a residual proportion (6.3%) of the compound No. 8, elution using $CH_2Cl_2/CH_3OH$ 100:2.7 (500 ml) gave 26 mg (evaporation residue) of the addition compound No. 10. According to HPLC (conditions as for compound No. 7), this substance is also a diaddition product consisting of 3 regioisomers in proportions of 27.5:17.7:54.8% by area. The mass spectrum (FAB) shows a molecular mass M=916 (intense $M^\ominus$ peak at m/e 916 and $MH^\oplus$ peak at m/e 917); TLC ($CH_2Cl_2/C_2H_5OH$ 10:1) $R_F$: 0.38–0.40.

After elution of the diaddition compound No. 10, elution wag continued using $CH_2Cl_2/CH_3OH$ (20:1) and (10:1) (each 500 ml). This gave 31 mg of a substance as evaporation residue from which were obtained, after digestion with ether, filtration with suction and drying (50° C., 3 mbar), 20 mg of diaddition compound No. 11 which was uniform according to TLC ($CH_2Cl_2/C_2H_5OH$ 10:1). According to HPLC (conditions as for compound No. 7) this substance consists of 27.5% (by area) of two regioisomeric diadducts, which are also present in the diaddition compound No. 10, and 72.5% (by area) of the diaddition compound No. 11. The C,H,N analysis and the mass spectrum show that these are diadducts.

Elemental analysis: found C 89.5H 2.5H 6.3%. The IR spectrum of this diaddition compound No. 11 is shown in FIG. 13.

The mass spectrum (FAB) shows a molecular mass M=916 (intense $M^\ominus$ peak at m/e 916 and $MH^\oplus$ peak at m/e 917); TLC ($CH_2Cl_2/C_2H_5OH$ 10:1) $R_F$: 0.28 to 0.30.

EXAMPLE 16

Under a blanket of nitrogen, a solution of 2907 mg of $C_{60/70}$ (97.25: 2.75) in 1200 ml of toluene was admixed at room temperature with a solution of 5.0 g of N,N'-dimethylethylenediamine in 300 ml of toluene and the mixture was stirred for 19.7 days at 85° C. and 14.1 days at room temperature. The reaction mixture was then filtered through a filter aid and the filtrate was applied to or filtered through a Kieselgel S(0.063 to 0.2 mm)-toluene column (H: 64; φ3.4 cm). After the filtered reaction solution had been drawn in, elution was continued using 500 ml of toluene and 500 ml of $CH_2Cl_2$. The first 2500 ml of eluate contained (after evaporation in vacuo, digestion of the residue in 40 ml of ether, filtration with suction and drying) 115 mg ($\equiv$4% of material used) of fullerene $C_{60>70}$. Subsequently, elution was continued using $CH_2Cl_2$ and $CH_2Cl_2/CH_3OH$ (100:0.5). After 1000 ml of substance-free eluate, 2500 ml of eluate (100:0.5) containing a brown-black moving zone were selected. After evaporation of the solvent from this fraction, digestion of the crystalline residue (490 mg) in 40 ml of ether and filtration with suction, there were obtained, after drying (4 hours, 50° C., 2 millibar), 462 mg of a crystalline product which is essentially pure monoaddition compound of N,N'-dimethylethylenediamine with $C_{60}$. The yield of this compound No. 12 is, based on reacted fullerene, 14.8% of theory.

Molecular formula: $C_{64}H_{10}N_2$ (MW 806.80) calc. C 95.28H 1.25N 3.47% found C 94.2H 1.1N 3.4%

The IR spectrum (recorded using an IR microscope. Powder on KBr) of this monoaddition compound No. 12 formed from N,N'-dimethylethylenediamine and $C_{60}$ is shown in FIG. 14.

The mass spectrum (FAB) shows a strong $MH^\oplus$ peak at m/e 807, which gives a molecular mass M=806.

Thin-layer chromatography (TLC) on Kieselgel 60/F 254, layer thickness 0.25 mm, from Riedel-de Haen, eluant: $CH_2Cl_2/C_2H_5OH$=10:1 (v/v): $R_F$: 0.53 to 0.58 (the monoaddition product runs closely behind $C_{60}$ and in front of the diaddition products.

This monoaddition product of N,N'-dimethylethylenediamine with $C_{60}$ ($\equiv$ referred to monoaddition compound No. 12) can be recrystallized from solvents and be further purified in this way. Suitable solvents for this purpose are dichlorobenzene, chlorobenzene and/or anisole and $CS_2$.

The new compound (No. 12) is sparingly soluble or essentially insoluble in benzene, toluene, $CHCl_3$, $CH_2Cl_2$ and $CH_3OH$, but readily soluble in $CS_2$.

After the above-described main product ($\equiv$ addition compound No. 12) had been eluted from the column, elution was continued using $CH_2Cl_2/CH_3OH$ (100:1 and 100:1.5) (each 1500 ml). After 300 ml of substance-free eluate, elution using 1200 ml (100:1) and 1500 ml (100:1.5) gave 1030 mg of a second addition compound.

After digestion with ether, filtration with suction and drying (50° C., 3 mbar) this gave 957 mg of diaddition compound (referred to as addition compound No. 13G) in crystalline form ($\equiv$27.7% yield based on reacted fullerene).

This addition compound No. 13G proved to be, according to TLC (eluant: $CH_2Cl_2/C_2H_5OH$=100:1.5), a mixture of 5 regioisomeric diaddition compounds. The presence of diadducts is shown by the elemental analysis and by the mass spectrum. The mass spectrum (FAB) shows a molecular mass M=892 by an intense $MH^\oplus$ peak at m/e 893.

Molecular formula (for diadducts 13G): $C_{68}H_{20}N_4$(MW 892.94) calc. C 91.47H 2.26N 6.27% found C 91.5H 2.2N 5.7%

The separation of this mixture into 5 pure diaddition compounds is described in Example 17.

After the diaddition compound No. 13G, consisting of 5 isomers, had been eluted from the column, elution was continued using 1 l (100:2) and a substance-free fraction was obtained. Further elution using $CH_2Cl_2/CH_3OH$ 100:3 and 100:4 (each 2 l) gave 1143 mg of redish brown-black eluate residue. This gave, after digestion with ether, filtration with suction and drying, 919 mg of a crystalline substance (≡26.6% yield based on reacted fullerene) which, according to TLC ($CH_2Cl_2/C_2H_5OH$ 100:1.5), consisted of 3 regioisomeric diadducts. These are referred to as diaddition compounds No. 14, 15 and 16. The presence of diadducts is shown by the elemental analysis and by the mass spectrum. The mass spectrum (FAB) shows a molecular mass M=892 by an intense $MH^⊕$ peak at m/e 893.

Molecular formula (for diadduct): $C_{68}H_{20}N_4$ (MW 892.94) calc. C 91.47H 2.26N 6.27% found C 90.6H 2.6N 5.8%

The chromatographic separation of this mixture into the pure diaddition compounds 14, 15 and 16 is described in Example 18.

EXAMPLE 17

Isolation in pure form of the 5 regioisomeric diadducts formed from N,N'-dimethylethylenediamine and $C_{60}$, described as a mixture in Example 16:

955 mg of the addition compound No. 13G obtained as described in Example 16 were dissolved at 80° C. in 400 ml of toluene and the solution was applied while warm to a Kieselgel 60 (grain size 0.04–0.064 mm)/toluene column (H =65; ɸ3.4 cm). The elution was carried out under 0.2 bar gauge pressure of $N_2$. After elution using 2 l of toluene, during which a substance-free eluate ran out, elution using $CH_2Cl_2$; $CH_2Cl_2/CH_3OH$ (100:0.1), (100:0.2), (100:0.3) and (100:0.35) (each 1.5 l) gave 72 mg of eluate residue which, after digestion with ether, filtration with suction and drying, gave 68 mg of pure diadduct No. 13A. The IR spectrum (KBr) of this diaddition compound No. 13A is shown in FIG. 15.

Continuing elution using (100:0.4) and (100:0.45) (2 and 3 l respectively) gave 123 mg of eluate residue which, processed as above, gave 114 mg of pure diaddition compound No. 13B. The IR spectrum (KBr) of this compound No. 13B is shown in FIG. 16.

Further elution using 1 l (100:0.45), 4 l (100:0.5) and 1 l (100:0.55) gave, after evaporation of the solvents, 328 mg of eluate residue. From this were obtained, after the above-described procedure, 317 mg of pure crystalline diaddition compound No. 13. The IR spectrum (KBr) of this compound No. 13 is shown in FIG. 17.

Further elution using 2 l each of $CH_2Cl_2/CH_3OH$ (100:1) and (100:2) gave 112 mg of eluate residue which, processed as above, gave 110 mg of pure crystalline diaddition compound No. 13C. The IR spectrum (KBr) thereof is shown in FIG. 18.

Further elution using 2 l each of (100:3) and (100:5) produced 225 mg of eluate residue, which, after processing as described above, gave 201 mg of pure, dark red-brown, crystalline diaddition compound No. 14. The IR spectrum (KBr) thereof is shown in FIG. 19.

TLC (Kieselgel 60/F254, layer thickness 0.25 mm; eluant: $CH_2Cl_2/C_2H_5OH$=100:1.5): the diaddition compounds No. 13A to No. 13C have the following $R_F$ values:

| No. | 13A | 13B | 13 | 13C |
|---|---|---|---|---|
| $R_F$: | 0.17–0.20 | 0.11–0.14 | 0.07–0.10 | 0.05–0.07 |

EXAMPLE 18

Isolation in pure form of the 3 regioisomeric diaddition products No. 14, No. 15 and No. 16 formed from N,N'dimethylethylenediamine and $C_{60}$ described as a mixture in Example 16:

919 mg of the diaddition compounds No. 14, 15 and 16 obtained as a mixture as described in Example 16 were dissolved at 80° C. in 500 ml of toluene, and the solution was applied while warm to a Kieselgel 60 (grain size 0.04–0.064 mm)/toluene column (H=45; ɸ3.2 cm). The elution was carried out under 0.2 bar gauge pressure of $N_2$. After elution using 200 ml of toluene and 1 l each of $CH_2Cl_2/CH_3OH$ (100:0.5) and (100:1), during which substance-free eluate ran out, elution using 2 l (100:1) gave 130 mg of eluate residue which, after digestion with ether, filtration with suction and drying (4 hours, 3–5 mbar) gave 121 mg of TLC-pure diaddition compound No. 14.

Continued elution using 1 l (100:1) produced, after evaporation, 98 mg of eluate residue which, after processing as described above, gave 83 mg of TLC-pure diaddition compound No. 15. The IR spectrum (KBr) of this diaddition compound No. 15 is shown in FIG. 20.

Further elution using 1 l of $CH_2Cl_2/CH_3OH$ (100:1.5), 1 l (100:1.75) and 1 l (100:2) gave, after evaporation, 300 mg of eluate residue which, after processing as described above, gave 279 mg of product which consisted of the diadducts No. 15 and No. 16. Further elution using 1 l of (100:3) produces 210 mg of eluate residue which, after processing as described above, gave 180 mg of TLC-pure diaddition compound No. 16. The IR spectrum (KBr) thereof is shown in FIG. 21.

TLC (Kieselgel 60/F254, layer thickness 0.25 mm; eluant: $CH_2Cl_2/C_2H_5OH$=100:4): the diaddition compounds No. 14–No. 16 have the following $R_F$ values:

| No. | 14 | 15 | 16 |
|---|---|---|---|
| $R_F$: | 0.11–0.12 | 0.09–0.11 | 0.04–0.06 |

EXAMPLE 19

Using a similar procedure to Example 16, a solution of 727 mg of $C_{60/70}$ (97.25:2.75) in 300 ml of toluene was admixed with a solution of 1.16 g of N,N'-diethylethylenediamine in 50 ml of toluene and the mixture was stirred for 6 days at 85° C. and for 8 days at RT. The reaction mixture was then filtered. The washed and dried (5 hours at 50° C., 6 mbar) filter residue weighed 1.06 g and is a complex mixture of higher adducts (>2) of N,N'-diethylethylenediamine and $C_{60/70}$. The filtrate was applied to a Kieselgel S/toluene column (H=42; ɸ1.9 cm). The chromatography was carried out using a similar procedure to that described in Examples 1 and 16. After elution using 100 ml of toluene, during which 44 mg (≡6% of material used) of unreacted $C_{60/70}$ were recovered, elution using 80 ml of toluene gave (after evaporation of the toluene) 51 mg of eluate residue. After digestion with ether, filtration with suction and drying (4 hours at 50° C., 6 mbar) this gave 27 mg (≡3.4% yield, based on reacted fullerene) of TLC-pure, crystalline monoadduct of N,N'-diethylethylenediamine with $C_{60}$. This substance is referred to as addition compound No. 17.

Molecular formula: $C_{66}H_{14}N_2$ (MW 834.85) calc. C 94.95H 1.69N 3.36% found C 95.6H 1.9N 3.3%

The IR spectrum (KBr) of this compound No. 17 is shown in FIG. 22.

The mass spectrum (FAB) shows a strong $MH^{\oplus}$ and strong $M^{\ominus}$ peak at m/e 835 and m/e 834 respectively.

TLC (eluant: $CH_2Cl_2/C_2H_5OH$ 10:1): $R_F$=0.68–0.70

TLC (eluant: toluene): $R_F$=0.30–0.32

EXAMPLE 20

Using a similar procedure to Example 16, a solution of 1211 mg of $C_{60/70}$ (97.25:2.75) in 500 ml of toluene was admixed with a solution of 2.06 g of N,N'-dimethyltrimethylenediamine in 80 ml of toluene and the mixture was stirred for 4.7 days at 80°–82° C. and for 12.2 days at RT. The reaction mixture was then filtered. The washed and dried filter residue weighed 126 mg and is presumably a complex mixture of higher (>2) adducts of N,N'-dimethyl-1,3-propylenediamine with $C_{60/70}$. The filtrate was applied to a Kieselgel S/toluene column (H=90; φ2.9 cm). The chromatography was carried out using a similar procedure to that described in Examples 1, 16 and 19. After elution using 600 ml of toluene, during which 403 mg (=33.3% of material used) of unreacted $C_{60/70}$ were recovered, further elution using 2.6 l of toluene and 1 l of $CH_2Cl_2$ gave, after evaporation of the solvents, 260 mg of eluate residue. After digestion with ether, filtration with suction and drying (4 hours at 50° C., 4–6 mbar), this gave 189 mg(=20.5% yield, based on reacted fullerene) of TLC-pure, crystalline monoadduct of N,N'-dimethyl-l-1,3-propylenediamine with $C_{60}$. This substance is referred to as addition compound No. 18.

Molecular formula: $C_{65}H_{12}N_2$ (MW 820.83) calc. C 95.11H 1.47N 3.41% found C 94.8H 1.5N 3.4%

The IR spectrum (KBr) of this compound No. 18 is shown in FIG. 23. The mass spectrum (FAB) shows a strong $MH^{\oplus}$ and a strong $M^{\ominus}$ peak at m/e 821 and m/e 820 respectively. TLC (eluant: $CH_2Cl_2/C_2H_5OH$ 10:1): $R_F$=0.68–0.70.

EXAMPLE 21

Using a procedure similar to Example 16, a solution of 2180 mg of $C_{60/70}$ (97.25:2.75) in 900 ml of toluene was admixed with a solution of 2225 mg of N-methylethylenediamine in 150 ml of toluene and the mixture was stirred for 3.1 days at 70°–73° C. and 2.6 days at RT. The reaction solution was then filtered and applied to a Kieselgel 60 (grain size 0.04–0.063 mm) toluene column (H=46 cm, φ4.8 cm). The chromatography was carried out under 0.2 bar gauge pressure of $N_2$ in a similar manner to Examples 1, 16 and 19. After elution using 1 l of toluene and 0.5 l of $CH_2Cl_2$, during which 137 mg (=6.3% of material used) of unreacted $C_{60/70}$ were recovered, further elution using 2 l each of $CH_2Cl_2/CH_3OH$ (100: 0.25) (100:0.5) and (100:0.75) gave an eluate residue of 13 mg which, after digestion in ether, filtration with suction and drying, gave 10 mg of a brown substance. Continued elution using 3 l (100:1), 1 l (100:1.5) and 2 l (100:2) produced, after evaporation of the solvents, 807 mg of eluate residue which, after digestion with 15 ml of ether, filtration with suction and drying (4 hours at 50° C., 3–6 mbar), gave 794 mg (=35.3% yield based on conversion) of crystalline, TLC-pure monoadduct of N-methyldiamine with $C_{60}$ (formula II: $R^1$=—$(CH_2)_2$—, $R^2$=$CH_3$, $R^3$=H). This monoadduct is referred to as addition compound No. 19.

Molecular formula: $C_{63}H_8N_2$ (MW 792.77) calc. C 95.54H 1.02N 3.53% found C 94.6H 1.0N 3.5%

The IR spectrum (KBr) of this compound No. 19 is shown in FIG. 24.

The mass spectrum (FAB) shows a strong $MH^{\oplus}$ and $M^{\ominus}$ peak m/e 793 and m/e 792 respectively. TLC (eluant: $CH_2Cl_2/C_2H_5OH$ 100:3): $R_F$=0.21–0.22.

EXAMPLE 22

Using a procedure similar to Example 16, a solution of 2720 mg of $C_{60/70}$ (97.75:2.25) in 1350 ml of toluene was admixed with a solution of 2224 mg of N-methylethylenediamine in 100 ml of toluene and the mixture was stirred for 2.5 days at 65° C. and 3.5 days at room temperature. The reaction solution was then filtered and applied to a Kieselgel 60 (grain size 0.043–0.060 mm)-toluene column (H=52 cm, φ3.6 cm). The chromatography was carried out under 0.25 bar gauge pressure of $N_2$ in a similar manner to Examples 1, 16 and 19. After elution using 1.2 l of toluene, during which 102 mg (=3.8% of material used) of unreacted $C_{60/70}$ were recovered, further elution using 1 l of toluene and 2 l of toluene/$CH_3OH$ (100:1) gave 47 mg of a substance which was not characterized in more detail. Continued elution using 2 l each of toluene/$CH_3OH$ (100:1) and (100:1.5) produced, after evaporation of the solvents, 2400 mg of eluate residue which, after digestion with ether, filtration with suction and drying (4 hours at 50° C., 3–6 mbar), gave 2075 mg (72% yield based on conversion) of crystalline, TLC-pure monoadduct of N-methylethylenediamine with $C_{60}$ (addition compound No. 19, cf. Example 21).

EXAMPLE 23

Using a procedure similar to Example 16, a solution of 2290 mg of $C_{60/70}$ (97.75:2.25) in 1000 ml of toluene was admixed with a solution of 2556 mg of a 98%-pure N-ethylethylenediamine in 80 ml of toluene and the mixture was stirred for 3.15 days at 68° C. and 4.65 days at room temperature. The reaction solution was then filtered and applied to a Kieselgel 60 (grain size 0.043–0.060 mm)-toluene column (H=52 cm, φ3.6 cm). The chromatography was carried out under 0.35 bar gauge pressure of $N_2$ in a similar manner to Examples 1, 16 and 19. After elution using 2.1 l of toluene, during which 260 mg (=11.4% of material used) of unreacted $C_{60/70}$ were recovered, further elution using 2 l each of toluene/$CH_3OH$ (100: 1), (100:1.25) and (100:1.50) gave, after evaporation of the solvents, 1400 mg of eluate residue. After digestion with ether, filtration with suction and drying (4 hours at 50° C., 3–6 mbar), this gave 1309 mg (57.6% yield based on conversion) of crystalline, TLC-pure monoadduct of N-ethylethylenediamine with $C_{60}$ ( formula II: $R^1$=—$(CH_2)_2$—, $R^2$=$C_2H_5$, $R^3$=H). This monoadduct is referred to as addition compound No. 20.

Molecular formula: $C_{64}H_{10}N_2$ (MW 806.80) calc. C 95.28H 1.25N 3.47% found C 92.6H 1.3N 3.4%

The IR spectrum (KBr) of this compound No. 20 is shown in FIG. 25.

The mass spectrum (FAB) shows a strong $MH^{\oplus}$ and $M^{\ominus}$ peak at m/e 807 and m/e 806 respectively. TLC (eluant: $CH_2Cl_2/C_2H_5OH$ 100:4): $R_F$=0.46–0.48.

EXAMPLE 24

Using a procedure similar to Example 16, a solution of 648 mg of $C_{60/70}$ (97.75:2.25) in 275 ml of toluene was admixed with a solution of 986 mg of cis-1,2-diaminocyclohexane in 10 ml of toluene and the mixture was stirred for 2.9 days at 68°–70° C. and for 4.9 days at room temperature. The reaction solution was then filtered and applied to a Kieselgel 60 (grain size 0.043–0.06 mm)-toluene acid (H=40 cm, φ2.5 cm). The chromatography was carried out under 0.3 bar gauge pressure of $N_2$ in a similar manner to Examples 1, 16 and 19. After elution using 0.55 l of toluene, during which 71 mg (=11% of material used) of unreacted $C_{60/70}$ were recovered, further elution using 2 l of toluene gave, after evaporation of the solvent, an eluate residue of 150 mg which, after digestion in ether, filtration with suction and drying, gave 140 mg (=21% yield based on conversion) of crystalline, TLC-pure monoadduct of cis-1,2-diaminocyclohexane with $C_{60}$ (formula II: $R_1=$

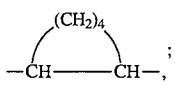

$R^2$, $R^3$=H). This monoadduct is referred to as addition compound No. 21.

Molecular formula: $C_{66}H_{12}N_2$ (MW 832.84) calc. C 95.18H 1.45N 3.36% found C 94.5H 1.5N 3.3%

The IR spectrum (KBr) of this compound No. 21 is shown in FIG. 26.

The mass spectrum (FAB) shows a strong $M^{\ominus}$ peak at m/e 832. TLC (eluant: $CH_2Cl_2/C_2H_5OH$ 100:4): $R_F$=0.68–0.70.

EXAMPLE 25

Using a procedure similar to Example 16, a solution of 303 mg of $C_{60/70}$ (97.25:2.75) in 125 ml of toluene was admixed with a solution of 360 mg of ethylenediamine in 15 ml of toluene and the mixture was stirred for 7 days at 80° C. and for 21 days at RT. The reaction mixture was then filtered. The washed and dried filter residue weighed 348 mg and is presumably a complex mixture of higher adducts of ethylene diamine with $C_{60/70}$. The filtrate was applied to a Kieselgel S/toluene column (H=30, φ2.9 cm). The chromatography was carried out in a similar manner to that described in Examples 1, 16 and 19. After elution using 250 ml of toluene and 200 ml of $CH_2Cl_2$, during which 36 mg (=11.9% of material used) of unreacted $C_{60/70}$ were recovered, further elution using 250 ml of $CH_2Cl_2/CH_3OH$ (100:0.5), 1 l (100:1), 300 ml (100:1.5) and 300 ml (100:2) gave, after evaporation of the solvents, 43 mg of eluate residue. After digestion with ether, filtration with suction and drying (4 hours at 50° C., 3–6 mbar), this gave 39 mg (=13.5% yield, based on reacted fullerene) of a crystalline substance which, according to TLC, contains a small amount (<10%) of a byproduct. The elemental analysis and the mass spectrum show the strongly enriched main component to be a monoadduct of ethylenediamine with $C_{60}$. This substance is referred to as addition compound No. 22 (formula II: $R^1$=—$(CH_2)_2$—, $R^2$, $R^3$=H)

Molecular formula: $C_{62}H_6N_2$ (MW 778.75) calc. C 95.63H 0.78N 3.60% found C 89.8H 0.8N 3.6%

The IR spectrum (KBr) of this compound No. 22 is shown in FIG. 27.

The mass spectrum (FAB) shows a strong $MH^{\oplus}$ and strong $M^{\ominus}$ peak at m/e 779 and m/e 778 respectively. TLC (eluant: $CH_2Cl_2/C_2H_5OH$ 10:1): $R_F$=0.43–0.45 ($R_F$ of the byproduct present: 0.49–0.52).

EXAMPLE 26

Isolation of diaddition compounds of N-methylethylenediamine with $C_{60}$ by chromatography:

1 g of the substance which had been obtained after elution of the main part of the monoaddition compound No. 19 in the chromatography of a reaction mixture obtained as described in Examples 21 and 22, and which consisted of unseparated monoaddition compound No. 19 and diadducts of N-methylethyldiamine with $C_{60}$, was further separated by chromatography as follows.

The substance to be separated (1 g) was dissolved in 100 ml of $CS_2$ and applied to a Kieselgel 60 (grain size: 0.040–0.063 mm)—$CH_2Cl_2$ column (H=30 cm, φ3.4 cm). The chromatography was carried out under 0.3 bar gauge pressure of $N_2$ in a similar manner to Examples 1, 16 and 19. After elution using 3 l of $CH_2Cl_2$ and 2 l each of $CH_2Cl_2/CH_3OH$ (100:0.1) and (100:0.2), during which substance-free eluates were obtained, further elution with 2 l each of $CH_2Cl_2/CH_3OH$ (100:0.2) and (100:0.3) and 1 l (100:0.3) gave, after evaporation of the solvents, 659 mg of eluate residue. This gave, after digestion with ether, filtration with suction and drying, 586 mg of TLC-pure monoaddition compound (addition compound No. 19; formula II: $R^1$=—$(CH_2)_2$—, $R^2$=$CH_3$, $R^3$=H). Elution was continued using $CH_2Cl_2/CH_3OH$ (100:3). The next fraction (0.5 l of eluate) left, after evaporation, 208 mg of residue which, treated as described above, gave, after drying, 195 mg of diaddition compound of N-methylethylenediamine with $C_{60}$ as described by formula III: $R^1$=—$(CH_2)_2$—, $R^2$=$C_3$, $R^3$=H). According to TLC (eluant: toluene/$CH_3OH$ 100:1), this substance consists of five regioisomeric diaddition compounds. This substance is referred to as diaddition compound No. 23G.

Molecular formula: $C_{66}H_{16}N_4$ (MW 864.89) calc. C 91.66H 1.86N 6.48% found C 89.2H 2.4N 6.2%

The mass spectrum (FAB) of this substance shows a strong $MH^{\oplus}$ and strong $M^{\ominus}$ peak at m/e 865 and m/e 864 respectively.

The next fraction (0.5 l of eluate) gave, after evaporation and similar treatment of the eluate residue as for previous fractions, 19 mg of diadduct after drying (according to TLC this has a somewhat different composition with regard to the regioisomers than does the previously eluted diadduct fraction). The following fraction (1 l of eluate) left, after similar treatment to that described above, 33 mg of a mixture of regioisomeric diadducts in which the more polar regioisomers are, according to TLC, present in greater amounts than in the previous fractions.

On further elution using 1 l of $CH_2Cl_2/CH_3OH$ (20:1), a dark zone was eluted and after evaporation, digestion of the eluate residue with ether, filtration with suction and drying there were obtained 28 mg of a diadduct which, according to TLC, contained one component (regioisomer) in greatly enriched form.

Molecular formula: $C_{66}H_{16}N_4$ (MW 864.89) calc. C 91.66H 1.86N 6.48% found C 89.5H 2.5N 6.3%

The mass spectrum (FAB) of this substance shows a strong $MH^{\oplus}$ peak at m/e 864. TLC (eluant: $CH_2Cl_2/C_2H_5OH$ 10:1): $R_F$=0.30–0.36. This substance is referred to as diaddition compound No. 23K. The IR spectrum (KBr) of this compound No. 23K is shown in FIG. 28.

EXAMPLE 27

Using a procedure similar to Example 16, a solution of 545 mg of $C_{70/60}$ (96.7:3.3) in 500 ml of toluene was admixed with a solution of 447 mg of N-methylethylenediamine in 20 ml of toluene and the mixture was stirred for 4.3 days at 79°–80° C. and for 2.7 days at room temperature. The reaction mixture was then filtered and applied to a Kieselgel 60 (grain size 0.04–0.063 mm)-toluene column (H=75 cm, φ2.5 cm). The chromatography was carried out at 0.35 bar gauge pressure of $N_2$ in a similar manner to Examples 1, 16 and 19. After elution using 0.7 l of toluene, during which 155 mg (=28.4% of material used) of unreacted $C_{70}$ were recovered, further elution using 1 l of toluene/$CH_3OH$ (100: 0.5); 1.3 l (100:0.75); 0.3 l (100:1) and 1 l (100:1.5) gave, after evaporation of the solvents, an eluate residue of 255 mg which, after digestion with 15 ml of ether, filtration with suction and drying (4 hours at 50° C., 3–6 mbar), gave 230 mg (=56.5% yield based on fullerene conversion) of crystalline, TLC-pure monoadduct of N-methylethylenediamine with $C_{70}$.

This monoadduct is referred to as addition compound No. 24.

Molecular formula: $C_{73}H_8N_2$ (MW 912.88) calc. C 96.05H 0.88N 3.07% found C 93.8H 1.3N 3.0%

The IR spectrum (KBr) of this compound No. 24 is shown in FIG. 29.

The mass spectrum (FAB) shows a strong $MH^\oplus$ and strong $M^\ominus$ peak at m/e 913 and m/e 912 respectively. TLC (eluant: $CH_2Cl_2/C_2H_5OH$ 10:1): $R_F$=0.56–0.66.

EXAMPLE 28

Using a procedure similar to Example 16, a solution of 234 mg of $C_{60/70}$ (97.75:2.25) in 126 ml of toluene was admixed with a solution of 27.3 mg (0.317 mmol) of piperazine and 67.3 mg (0.6 mmol) of 1,4-diazabidyclo [2.2.2]octane in 125 ml of toluene and the mixture was stirred for 16.7 days at room temperature. The reaction solution was then applied to a Kieselgel S (grain size 0.063–0.20 mm)—$CH_2Cl_2$ column (H=21 cm, φ2.9 cm). After elution using 1 l of $CH_2Cl_2$, during which 158 mg (=67.5% of material used) of unreacted $C_{60/70}$ were recovered, further elution using 0.5 l each of $CH_2Cl_2/CH_3OH$ (100:0.5), (100:1), and (100:2) gave, after evaporation of the solvents, 82 mg of eluate residue. After digestion with ether, filtration with suction and drying (4 hours, 50° C., 4–7 mbar), this gave 60 mg (70.4% yield based on $C_{60/70}$ conversion) of crystalline, TLC-pure addition compound No. 1 (formula II: $R^1$ and $R^2$—$R^3$=—$(CH_2)_2$—). After elution of this addition compound No. 1, more polar eluants gave virtually only traces of higher addition products (<2 mg).

We claim:

1. An addition compound obtainable by reaction of a diamine of the formula I,

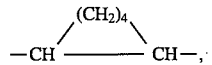

where $R^1$ is $(C_2–C_4)$-alkylene or 1,2- or 1,3-cyclo-$(C_3–C_7)$-alkylene and $R^2$ and $R^3$ which are identical or different, are $(C_1–C_3)$-alkyl or hydrogen or $R^2$ and $R^3$ together are $(C_2–C_4)$-alkylene, with fullerene $C_{60}$ and/or $C_{70}$, and also its acid-addition salts, with the proviso that addition compounds obtainable by reaction of a diamine of the formula I in which $R^1$=$C_2$-alkylene and $R^2$ and $R^3$= hydrogen with fullerene $C_{60}$ are excluded.

2. A monoaddition compound as claimed in claim 1.

3. A diaddition compound as claimed in claim 1.

4. An addition compound as claimed in claim 1, obtainable by reaction of N,N'-dimethylethylenediamine, piperazine, homopiperazine or N-methylethylenediamine with fullerene $C_{60}$ and/or $C_{70}$.

5. A monoaddition compound as claimed in claim 4, obtainable by addition reaction of N,N'-dimethylethylenediamine, piperazine, homopiperazine or N-methylethylenediamine with fullerene $C_{60}$.

6. A diaddition compound as claimed in claim 4, obtainable by addition reaction of N,N'-dimethylethylenediamine, piperazine, homopiperazine or N-methylethylenediamine with fullerene $C_{60}$.

7. An addition compound as claimed in claim 1, obtained by reacting a diamine of the formula I, in which $R^1$ is —$(CH_2)_2$—, —$(CH_2)_3$— or

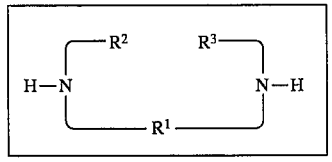

$R^2$ and $R^3$ are, independently of one another, hydrogen, —$CH_3$ or —$C_2H_5$ or $R^2$ and $R^3$ together are —$(CH_2)_2$— or —$(CH_2)_3$—, with fullerene $C_{60}$, fullerene $C_{70}$ or mixtures thereof.

8. An addition compound as claimed in claim 7, wherein said reacting is carried out using a fullerene mixture which contains at least 95% of fullerenes selected from the group consisting of fullerene $C_{60}$, fullerene $C_{70}$ or mixtures thereof.

9. An addition compound as claimed in claim 7, wherein said reacting is carried out using a fullerene mixture comprising greater than 95% fullerene $C_{60}$.

10. An addition compound as claimed in claim 7, wherein said reacting is carried out using a fullerene mixture having a purity greater than 95% fullerene $C_{70}$.

11. A process for preparing an addition compound as claimed in claim 1, which comprises reacting the diamine of the formula I, as shown in claim 1, with fullerene $C_{60}$ and/or fullerene $C_{70}$ in an inert solvent.

12. The process as claimed in claim 11, wherein the diamine of the formula I and fullerene $C_{60}$ and/or $C_{70}$ are used in a ratio of from 0.5 to 20.0.

13. The process as claimed in claim 11, wherein fullerene $C_{60}$ and/or $C_{70}$ is used in a concentration of from 0.6 to 5.5 millimole per liter.

14. The process as claimed in claim 11, wherein the solvent used is benzene, toluene, chlorobenzene, dichlorobenzene and/or anisole.

15. The process as claimed in claim 11, wherein the reaction is carried out in the presence of a tertiary mine.

16. The process as claimed in claim 11, wherein the reaction is carried out in a temperature range from –30° C. to 300° C.

17. The process as claimed in claim 11, wherein said fullerene is reacted in dissolved form.

18. The process as claimed in claim 8, wherein $R^1$ is —$(CH_2)_2$—, —$(CH_2)_3$— or

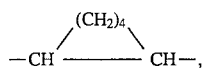

$R^2$ and $R^3$ are, independently of one another, hydrogen, —$CH_3$ or —$C_2H_5$ or $R^2$ and $R^3$ together are —$(CH_2)_2$— or —$(CH_2)_3$—.

19. The process as claimed in claim 11, wherein the reacting is carried out at a temperature from 0° C. to 160° C.

20. A method of using the addition compound as claimed in claim 1, comprising the step of transmitting electrical energy through said compound.

* * * * *